US010748319B1

(12) United States Patent
Tao et al.

(10) Patent No.: US 10,748,319 B1
(45) Date of Patent: Aug. 18, 2020

(54) COMPOSITE RADIOGRAPHIC IMAGE THAT CORRECTS EFFECTS OF PARALLAX DISTORTION

(71) Applicant: Radlink, Inc., El Segundo, CA (US)

(72) Inventors: Wenchao Tao, Los Angeles, CA (US); Ning Xuan, Torrance, CA (US)

(73) Assignee: RADLINK, INC., El Segundo, CA (US)

( * ) Notice: Subject to any disclaimer, the term of this patent is extended or adjusted under 35 U.S.C. 154(b) by 0 days.

(21) Appl. No.: 16/851,545

(22) Filed: Apr. 17, 2020

Related U.S. Application Data

(63) Continuation-in-part of application No. 16/212,065, filed on Dec. 6, 2018, and a continuation-in-part of
(Continued)

(51) Int. Cl.
*G06T 11/60* (2006.01)
*G06T 5/00* (2006.01)
(Continued)

(52) U.S. Cl.
CPC .............. *G06T 11/60* (2013.01); *G06T 5/001* (2013.01); *G06T 5/006* (2013.01); *G06T 5/50* (2013.01);
(Continued)

(58) Field of Classification Search
None
See application file for complete search history.

(56) References Cited

U.S. PATENT DOCUMENTS

| 6,078,699 A | 6/2000 | Lobregt |
| 6,097,833 A | 8/2000 | Lobregt |

(Continued)

FOREIGN PATENT DOCUMENTS

| JP | 2015501174 A | * | 1/2015 |
| WO | WO 2009/153789 | | 12/2009 |

(Continued)

OTHER PUBLICATIONS

Machine Translation JP 2015-501174 A (Year: 2015).*
(Continued)

*Primary Examiner* — Michelle M Entezari
(74) *Attorney, Agent, or Firm* — Cislo & Thomas, LLP; Kelly W. Cunningham

(57) ABSTRACT

The present disclosure is directed toward systems and methods for generating a composite radiographic image that corrects effects of parallax distortion. A sequence of radiographic images—including a series of discrete exposures or image frames from a fluoroscopic procedure—may be acquired using a C-arm apparatus. An exemplary method may include receiving a plurality of radiographic image frames pertaining to a patient, identifying a region of interest on the image frames, cropping the region of interest from a plurality of image frames, selecting a plurality of sequential portions of cropped image frames, and stitching together the selected portions to form a composite image that corrects effects of parallax distortion and displaying a three-dimensional image of a part of the patient according to the orientation of the patient calculated from this two-dimensional intra-operative radiographic imaging information.

20 Claims, 19 Drawing Sheets

Related U.S. Application Data application No. 15/708,821, filed on Sep. 19, 2017, now Pat. No. 10,650,561.

(60) Provisional application No. 62/595,670, filed on Dec. 7, 2017, provisional application No. 62/396,611, filed on Sep. 19, 2016.

(51) Int. Cl.
*G06T 5/50* (2006.01)
*G06T 7/60* (2017.01)

(52) U.S. Cl.
CPC ...... *G06T 7/60* (2013.01); *G06T 2207/10121* (2013.01); *G06T 2207/30008* (2013.01)

(56) References Cited

U.S. PATENT DOCUMENTS

| | | | |
|---|---|---|---|
| 6,101,238 A | 8/2000 | Murthy | |
| 6,947,038 B1 | 9/2005 | Anh | |
| 7,327,865 B2 | 2/2008 | Fu | |
| 7,657,299 B2 | 2/2010 | Hulzenga | |
| 8,290,228 B2 | 10/2012 | Cohen | |
| 8,611,697 B2 | 12/2013 | Nathaniel | |
| 8,948,487 B2 * | 2/2015 | Sundar | G06T 3/0068 382/132 |
| 9,109,998 B2 | 8/2015 | Nathaniel | |
| 9,111,180 B2 | 8/2015 | Rappaport | |
| 9,554,728 B2 | 1/2017 | Manzke | |
| 9,582,882 B2 | 2/2017 | Chen | |
| 10,010,249 B1 | 7/2018 | Sadda | |
| 10,022,192 B1 | 7/2018 | Ummalaneni | |
| 10,271,817 B2 * | 4/2019 | Voigt | A61B 8/5223 |
| 10,433,914 B2 * | 10/2019 | Wollowick | A61B 34/10 |
| 10,448,901 B2 | 10/2019 | McVeigh | |
| 10,512,451 B2 * | 12/2019 | Mahfouz | A61B 34/10 |
| 2004/0071269 A1 | 4/2004 | Wang | |
| 2010/0014780 A1 | 1/2010 | Kalayeh | |
| 2011/0188726 A1 | 8/2011 | Nathaniel | |
| 2012/0076260 A1 | 3/2012 | Kitagawa | |
| 2014/0086394 A1 | 3/2014 | Batkilin | |
| 2014/0093154 A1 | 4/2014 | Penenberg | |
| 2015/0278988 A1 | 10/2015 | MacMillan | |
| 2015/0371431 A1 | 12/2015 | Korb | |
| 2015/0373263 A1 | 12/2015 | Georgiev | |
| 2016/0100909 A1 | 4/2016 | Wollowick | |
| 2017/0360578 A1 | 12/2017 | Shin | |
| 2020/0100751 A1 * | 4/2020 | Wollowick | A61B 6/12 |

FOREIGN PATENT DOCUMENTS

| | | | |
|---|---|---|---|
| WO | WO 2015/185503 | 12/2015 | |
| WO | WO-2017106357 A1 * | 6/2017 | A61B 6/5223 |

OTHER PUBLICATIONS

Zhang; "Parallax-tolerant image stitching," Proceedings of the IEEE Conference on Computer Vision and Pattern Recognition (2014).

Yaniv; "Long Bone Panoramas from Fluoroscopic X-ray Images," IEEE Transactions on Medical Imaging, 23.1, pp. 26-35 (2004).

Xiao-Chun; "An Efficient Medical Image Registration Algorithm Based on Gradient Descent," IEEE/ICME International Conference (2007).

Chen; "Ruler-based Automatic C-arm Image Stitching Without Overlapping Constraint," Journal of Digital Imaging, vol. 28 No. 4 (Aug. 2015).

Wang: "Parallax-free Intra-operative X-ray Image Stitching," Medical Image Analysis, vol. 14, pp. 674-689 (2010).

International Search Report, issued in corresponding international application PCT/US2017/0052219, dated Nov. 20, 2017.

International Preliminary Report on Patentability, issued in corresponding international application PCT/US2017/0052219, dated Mar. 19, 2019.

U.S. Appl. No. 14/481,810; Third-Party Submission; 11 pages, dated Sep. 28, 2016.

* cited by examiner

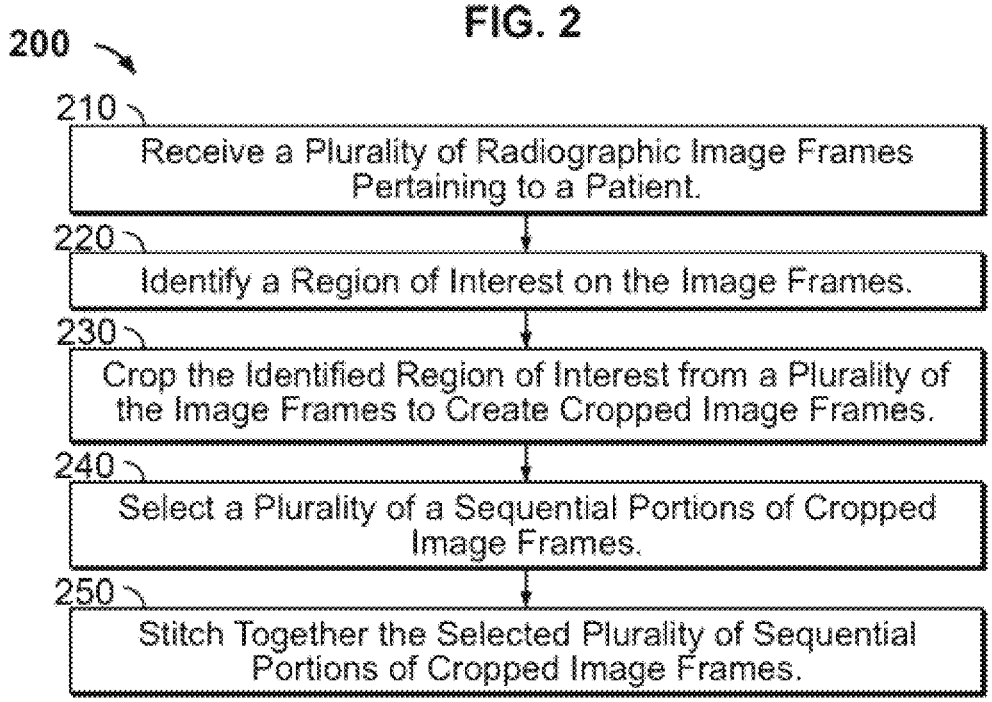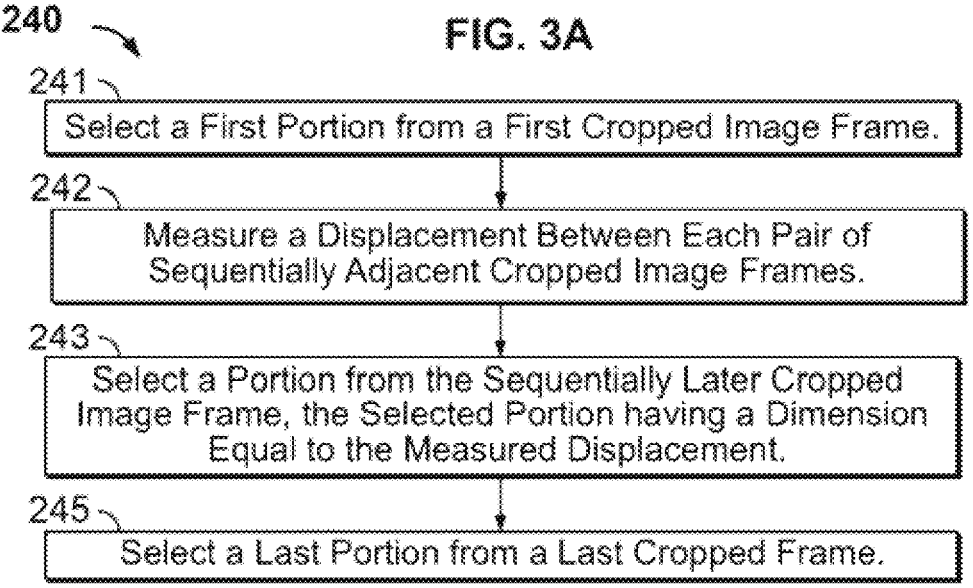

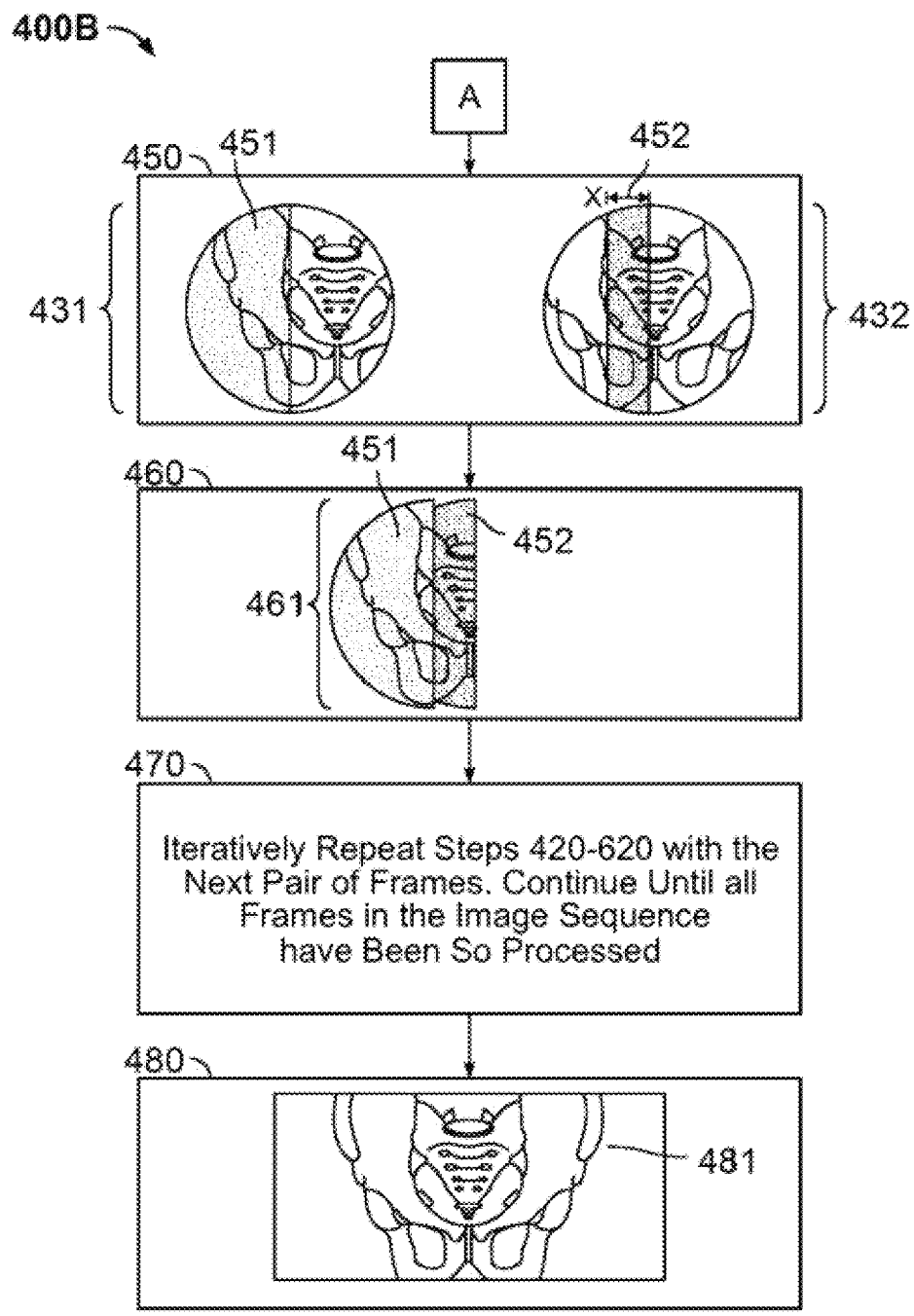

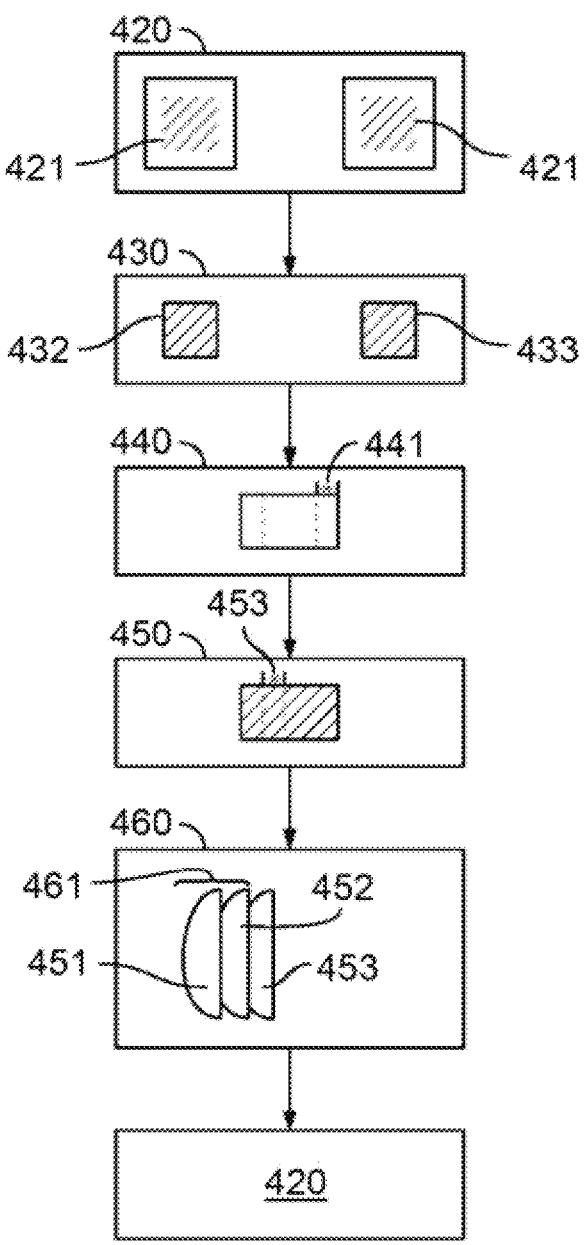

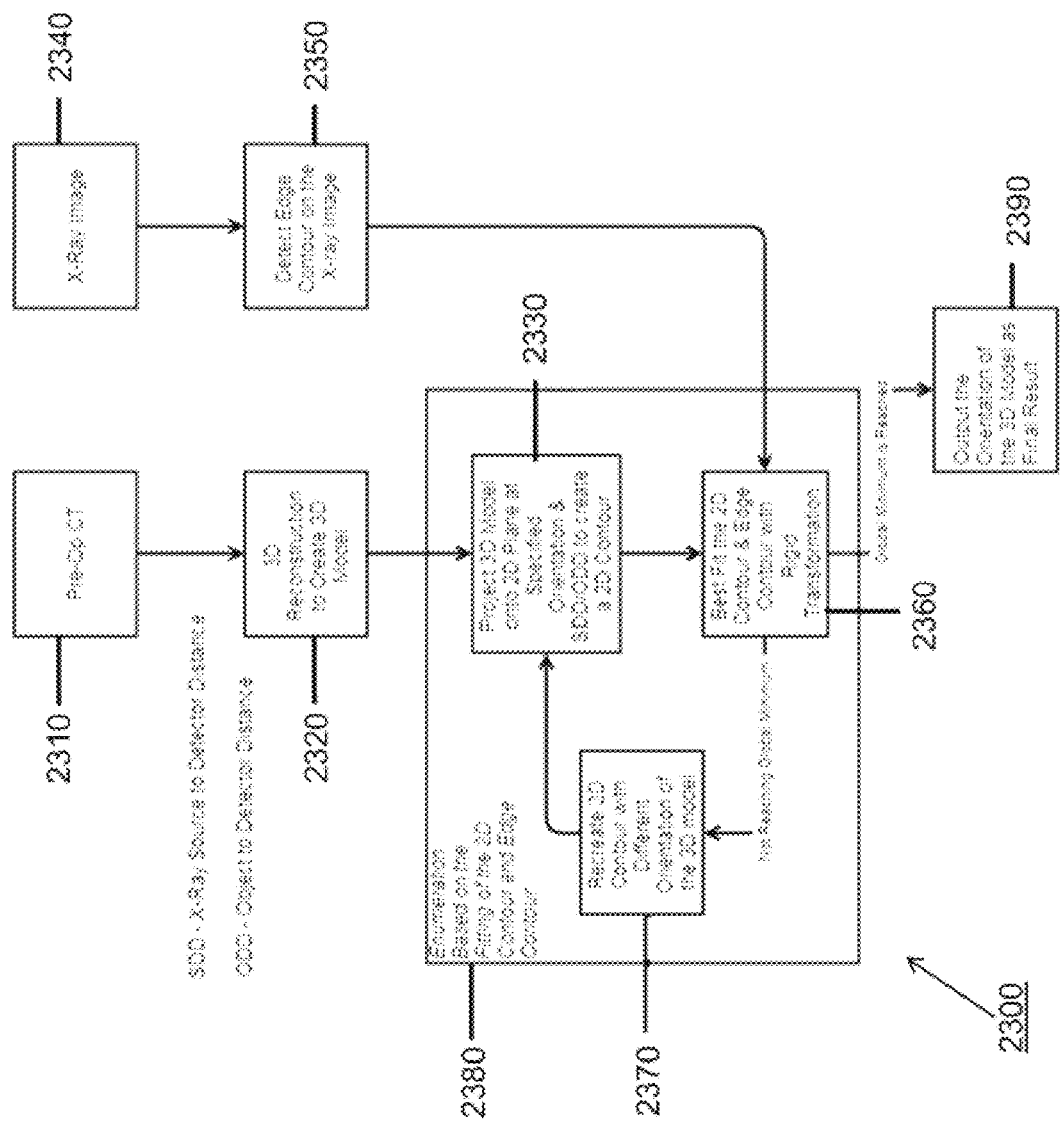

COMPOSITE RADIOGRAPHIC IMAGE THAT CORRECTS EFFECTS OF PARALLAX DISTORTION

CROSS-REFERENCES TO RELATED APPLICATIONS

This patent application claims is a continuation-in-part application to U.S. patent application Ser. No. 15/708,821, filed Sep. 19, 2017, which claims the benefit of U.S. Provisional Application No. 62/396,611, which was filed on Sep. 19, 2016; and this application is a continuation-in-part application to U.S. patent application Ser. No. 16/212,065, filed Dec. 6, 2018, which claims the benefit of U.S. Provisional Application No. 62/595,670, which was filed on Dec. 7, 2017. Each of the above-identified applications is, by this reference thereto, incorporated herein in their entireties.

TECHNICAL FIELD

The present disclosure relates to systems and methods to create a composite radiographic image that corrects effects of parallax distortion and help obtain a proper placement and positioning of a component such as an acetabular cup or a femoral component during a surgical procedure.

BACKGROUND

During certain surgical procedures, particularly orthopedic surgeries, it may be desired to obtain radiographic images before and even during surgery. Sometimes a radiographic image of a particularly wide or long body part, such as a pelvis or a femur, is taken. Often these images are used to take various measurements of the patient. For example, an orthopedic surgeon may take an intra-operative radiographic image of a patient's pelvis to, for example, measure a discrepancy in a patient's leg lengths. A common apparatus used to take such intra-operative images is a C-arm that includes an X-ray source and X-ray detector. However, a pelvis is often too wide to fit within the field of view of an image from a C-arm. Furthermore, distortions in the image, particularly parallax distortions near the ends of the field of view, may cause the accuracy of any measurements taken using such an image to be reduced.

There is a need for a system that allows a surgeon to view intra-operatively, for example, a full body part, such as a pelvis, that corrects effects of parallax distortion to allow the surgeon to make accurate intra-operative measurements.

SUMMARY

The present disclosure is directed to methods and systems to improve the quality and accuracy of intra-operative radiographic images, particularly of wide-view objects, by generating a composite image that corrects effects of parallax distortion and then displaying a three-dimensional projection of a region of the patient relative to this composite image. The method of the present disclosure may comprise acquiring a sequence of digital radiographic image frames, identifying a region of interest on the image frames, cropping the identified region of interest from a plurality of the image frames, and stitching together a plurality of selected portions of cropped image frames to create a composite image. The plurality of selected portions of cropped image frames may be selected by (1) selecting a sequentially first selected portion from a first cropped image frame; (2) iteratively selecting a plurality of interior selected portions by (a) measuring a displacement between each pair of sequentially adjacent cropped image frames and (b) selecting a portion from the sequentially later cropped image frame corresponding to the measured displacement; and (3) selecting a sequentially last portion from a last cropped image frame. Each selected middle portion may have a dimension that corresponds to the measured displacement. In an embodiment, each selected middle portion may be selected from the interior 25% of the field of view of the respective cropped image frame.

The sequence of radiographic images may be taken using a C-arm apparatus with an X-ray source and X-ray detector disposed thereon. In an embodiment, the sequence of radiographic images is a result of several (for example, five to ten) discrete exposures. In an embodiment, the sequence of radiographic images is a result of a fluoroscopic procedure generating a relatively larger number (for example, 25 to 75) of image frames. A surgeon may be able to use a composite image that corrects effects of parallax distortion according to an aspect of the present disclosure to take more accurate measurements, such as, for example, leg length discrepancy measurements, of a patient.

Then, the composite image is used with an initial three-dimensional image of a patient in a neutral position for generating a three-dimensional model corresponding to the spatial orientation of the composite image. A plurality of two-dimensional projections are scored by calculating the distance of the bony edge contour in the intra-operative imaging information to a corresponding contour in each two-dimensional projection and identifying a global minimum score. Calculating a transformation matrix for the two-dimensional projection having the global minimum score and displaying the three-dimensional image of the patient established thereby and optionally displaying a visual indication an intra-operative adjustment to be made to a component based on the adjustment factor to achieve a target component orientation.

BRIEF DESCRIPTION OF THE DRAWINGS

The foregoing and other features of the present disclosure will become more fully apparent from the following description, taken in conjunction with the accompanying drawings. Understanding that these drawings depict only several embodiments in accordance with the disclosure, they are, therefore, not to be considered limiting of its scope. The disclosure will be described with additional specificity and detail through use of the accompanying drawings.

In the drawings:

FIG. 2 depicts a flow chart presenting an exemplary method to generate a composite radiographic image that corrects effects of parallax distortion in accordance with an aspect of the present disclosure;

FIG. 3A presents an exemplary method for selecting constituent images to be formed into a composite image in accordance with an aspect of the present disclosure;

FIG. 4B depicts a second portion of an exemplary method for generating a composite radiographic image that corrects effects of parallax distortion in accordance with an aspect of the present disclosure;

FIG. 4C illustrates the iterative nature of at least a portion of an exemplary method for generating a composite radiographic image in accordance with an aspect of the present disclosure;

FIG. 15 is an exemplary flow chart diagram illustrating steps that may be taken to render one or more two-dimensional projections from a three-dimensional model of a portion of a patient in accordance with an embodiment of the present disclosure;

DETAILED DESCRIPTION

Figure 1:
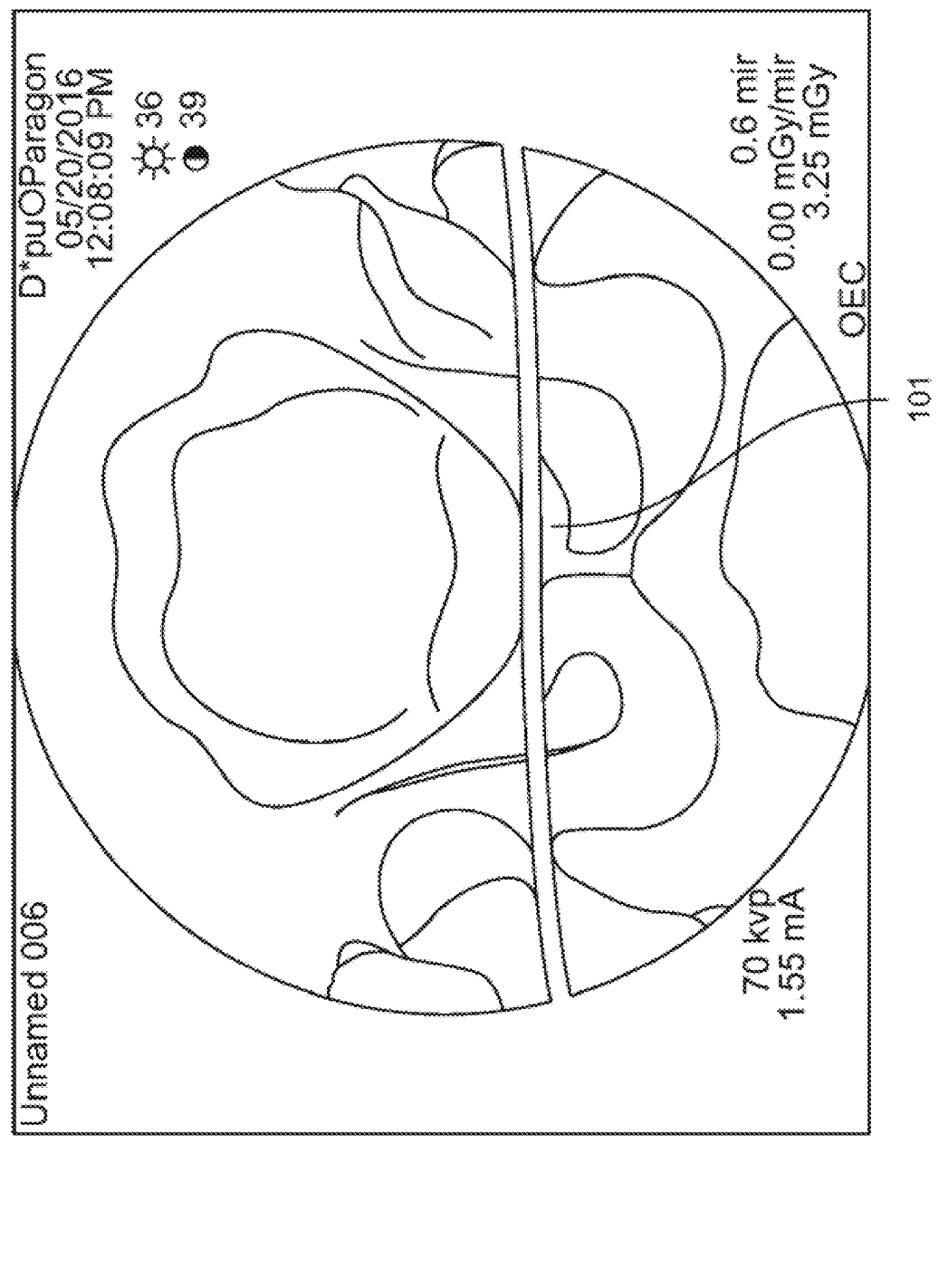
FIG. 1 presents a conventional radiographic image illustrating parallax distortion.

In the following detailed description, reference is made to the accompanying drawings, which form a part hereof. In the drawings, similar symbols typically identify similar components, unless context dictates otherwise. The illustrative embodiments described herein are not meant to be limiting. Other embodiments may be utilized, and other changes may be made, without departing from the spirit or scope of the subject matter presented here. It will be readily understood that the aspects of the present disclosure, as generally described herein and illustrated in the figures, may be arranged, substituted, combined, and designed in a wide variety of different configurations, all of which are explicitly contemplated and make part of this disclosure.

Digital radiographic two-dimensional images can be acquired by exposing X-ray sensors at a detector to X-rays from an X-ray source. When a patient is disposed between the X-ray source and the detector, digital radiographic images may be acquired and transmitted to a computer (via wired or wireless connection) for review, archiving, and/or enhancement. Acquired images can be saved in a variety of formats, such as tiff, j peg, png, bmp, dicom, and raw formatted images for both reading and writing.

Digital radiography offers numerous advantages over traditional X-ray methods. For example, digital radiography generates lower radiation levels than the levels required by traditional X-ray techniques using radiographic or phosphor film. Further, two-dimensional radiographic images may be viewed much quicker than traditional X-ray film due to reduced image acquisition time. The ability to digitally enhance digital X-ray images may further reduce radiation exposure levels.

The present disclosure is directed toward systems and methods for generating composite radiographic imaging information that corrects effects of parallax distortion. A sequence of radiographic images—including a series of discrete exposures or image frames from a fluoroscopic procedure—may be acquired using a C-arm apparatus. Conventional C-arm images have a limited view, precluding a member of a surgical team from viewing the entirety of a long structure, such as the width of a pelvis or length of a spine, in one image. The images that are captured often incorporate significant parallax distortions. Composite two-dimensional imaging information generated according to one of the exemplary methods described in fuller detail below, however, may allow a member of a surgical team to obtain a full view of a long structure in one image, and the composite image may correct effects of parallax distortion.

FIG. 1 presents a conventional radiographic image, and the effects of parallax distortion are clear from the image. The image 100 is an anteroposterior view of a portion of a pelvis in which a straight metal bar 101 was laid on the anterior side of a patient. In the image 100, the straight metal bar 101 appears rather curvy. The curves on straight metal bar 101 are the results of parallax distortion. Parallax distortion likewise affects the display of the patient structures being imaged and can cause inaccuracies in certain measurements that may be desired before or during an orthopedic surgery. More accurate measurements may allow members of the surgical team to complete certain aspects of orthopedic surgeries more efficiently, accurately, and confidently.

As used herein, the term "sequential" refers to the order in which a series of radiographic image frames are taken or selected, depending on the context. For clarity, a sequence of radiographic image frames, or sequential image frames, does not require that each and every image frame in a given set of image frames be selected or used but does indicate that the selected or used image frames maintain the relative order in which the image frames were taken or generated.

As used herein, the term "displacement" refers to the amount of offset between sequential image frames along a particular axis. A second image frame may have a displacement with regard to a first image frame, for example, due to movement of a C-arm apparatus with respect to an anatomical part being imaged.

FIG. 2 depicts a flow chart presenting an exemplary method 200 to generate the intra-operative composite radiographic imaging information to correct effects of parallax distortion in accordance with an aspect of the present disclosure. In an embodiment, a system, such as a computer system communicatively coupled to a C-arm apparatus, receives a plurality of radiographic image frames pertaining to a patient in step 210. The radiographic image frames may comprise a sequence of discrete exposures, or the radiographic image frames may comprise frames from a fluoroscopy procedure. The system or a user thereof may identify a region of interest on the image frames in step 220. For example, the region of interest may be a structure too large for a C-arm to capture in a single image, such as a pelvis or a spine. The identified region of interest may be cropped from a plurality of the image frames in step 230. A plurality of sequential portions of cropped image frames may be selected in step 240. The selected plurality of sequential portions of cropped image frames may be stitched together in step 250 to create a composite radiographic image that displays the entire large structure, and the composite image may correct effects of parallax distortion.

In a given image frame, there may be less distortion, including parallax distortion, in an interior part of the image frame than in an edge part of the image frame. Combining a plurality of relatively small-width portions from a plurality of image frames, with each portion being taken from an interior part of an image frame, may result in a wide-view composite image that corrects effects of parallax distortion. The effects of parallax distortion may become more pronounced at a location farther from the middle of the image frame. In an embodiment, each selected interior portion may be taken from an interior 25% of the respective image frame.

FIG. 3A presents a flow chart depicting an exemplary method 240 for selecting a plurality of sequential portions of cropped image frames generated in step 230. The portions of cropped image frames, once selected, become constituent images to be stitched together to form an intra-operative composite image, or composite two-dimensional imaging information. In an embodiment, method 240 may comprise selecting a sequentially first portion from a first cropped image frame 241. The selected sequentially first portion of step 241 may correspond to an edge part of a composite image. In an embodiment, the selected sequentially first portion of step 241 may comprise up to about half of the first cropped image frame. In an embodiment where the radiographic image frames are generated from a fluoroscopic procedure, the selected sequentially first portion of step 241 may comprise half of the first cropped image frame. In an embodiment where the radiographic image frames are generated from a series of discrete radiographic exposures, when the first cropped image frame and a sequentially next image frame are aligned to create partial overlap in the images, the selected sequentially first portion of step 241 may comprise a non-overlapped part of the first cropped image frame plus half of the overlapping region.

Still referring to FIG. 3A, method 240 may further comprise measuring a displacement between each pair of sequentially adjacent cropped image frames 242 with respect to a longitudinal axis of the anatomical part being imaged. For clarity, the measuring step 242 could include measuring a displacement with respect to a longitudinal axis of the anatomical part being imaged between every pair of adjacent cropped image frames generated by a C-arm and received in step 210. Alternatively, measuring step 242 could occur after a step of selecting all of the constituent cropped image frames to be used to create a composite image, in which case only a displacement with respect to a longitudinal axis of the anatomical part being imaged between adjacent selected sequential cropped image frames that will be used to create the intra-operative composite imaging information will be measured. In an embodiment, measuring step 242 may include applying intensity-based image registration using a gradient descent algorithm. In an embodiment, measuring step 242 may measure a displacement between two cropped image frames with respect to a longitudinal axis of the anatomical part being imaged, an axis orthogonal to the longitudinal axis of the anatomical part being imaged, and/or a rotational axis about the anatomical part being imaged. Method 240 may further comprise selecting an interior portion from the sequentially later cropped image frame 243. The sequentially later cropped image frame refers to the cropped image frame from the pair of sequentially adjacent cropped image frames in step 242 that occurs relatively later in the pair. Each selected interior portion from step 243 may be selected from an interior part of the sequentially later cropped image frame, as the sequentially later cropped image frame may be less distorted in an interior part of the image frame than near an edge of the image frame. Each selected interior portion from step 243, in a composite image, may be disposed in the interior part of the composite image, i.e., between the sequentially first portion from step 241 and a sequentially last portion. Each selected interior portion from step 243 may have a dimension corresponding to—and in an embodiment, equal to—a respective measured displacement from step 242. For example, if measuring step 242 measures a displacement between two cropped image frames with respect to a longitudinal axis of an anatomical part being imaged, a selected interior portion may have a width equal to the measured displacement between the two cropped image frames. In such a case, the length of the selected interior portion may have a height corresponding to the height of the sequentially later cropped image frame. A composite image may have a plurality of selected interior portions, with each selected interior portion being selected from a respective cropped image frame from a sequence of cropped image frames. Method 240 may further comprise selecting a sequentially last portion from a last cropped image frame 245. The selected sequentially last portion of step 245 may correspond to an edge part of a composite image. In an embodiment, the selected sequentially last portion of step 245 may comprise up to about half of the last cropped image frame.

In an embodiment, each selected interior portion may correspond to a measured displacement with respect to a longitudinal axis of an anatomical part being imaged from step 242. In an embodiment, each measured displacement may be about a few pixels of a digital image, and each selected interior portion may also be a few pixels in width. The width of the measured displacement may depend on the speed of movement of a C-arm apparatus and image-capturing frame rate. For example, if a C-arm apparatus is moved such that it takes about 10 seconds to move from one side of the region of interest to the other and the frame rate is set to 5 frames per second, the measured displacement may be between about 10-20 pixels. Accordingly, in such an embodiment, each selected interior portion may also be about 10-20 pixels wide. If, for example, each image frame is about 1,024 pixels wide, the width of each selected interior portion may correspond to about 1-2% of the width of the image frame from which it is taken.

Figure 3B:
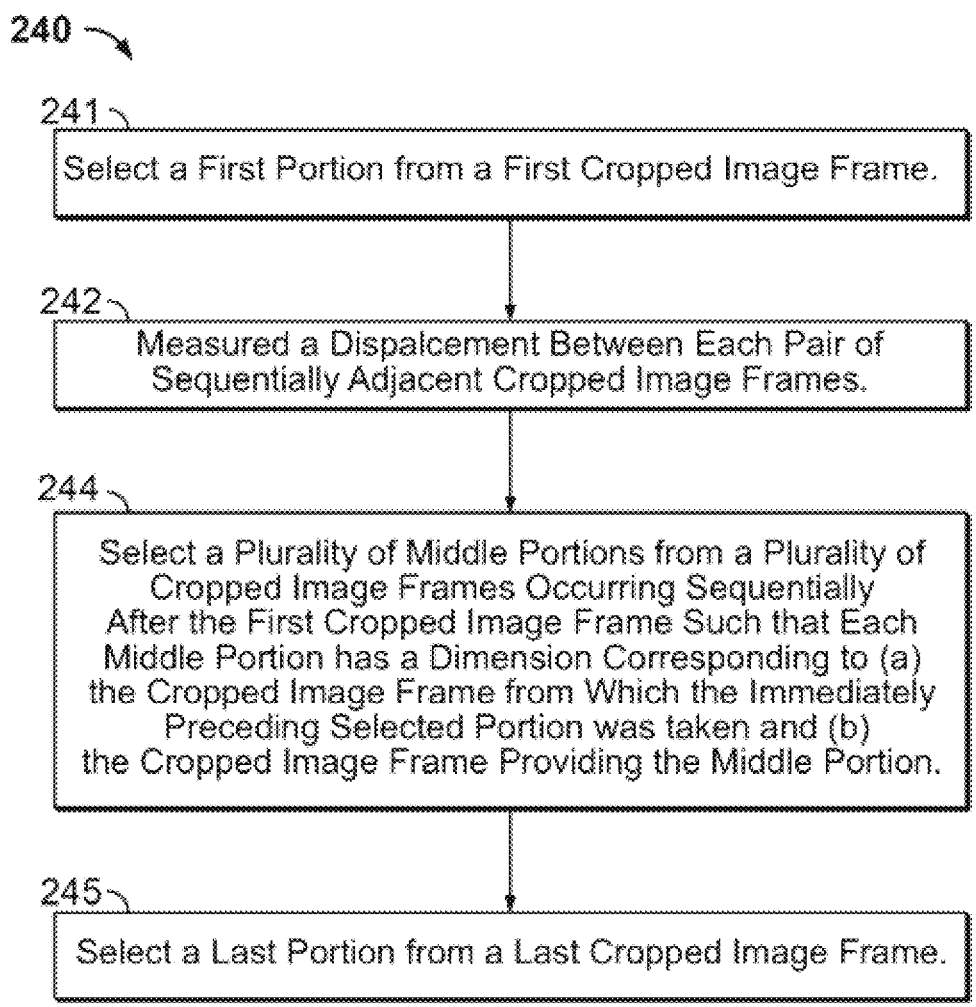
FIG. 3B presents an exemplary method for selecting constituent images to be formed into a composite image in accordance with an aspect of the present disclosure.

FIG. 3B presents a flow chart depicting an alternate exemplary method 240 for selecting a plurality of sequential portions of cropped image frames generated in step 230. The portions of cropped image frames, once selected, become constituent images to be stitched together to form a composite image. In an embodiment, method 240 may comprise selecting a sequentially first portion from a first cropped image frame 241. The selected sequentially first portion of step 241 may correspond to an edge part of an intraoperative composite image. In an embodiment, the selected sequentially first portion of step 241 may comprise up to about half of the first cropped image frame. In an embodiment where the radiographic image frames are generated from a fluoroscopic procedure, the selected sequentially first portion of step 241 may comprise half of the first cropped image frame. In an embodiment where the two-dimensional radiographic image frames are generated from a series of discrete radiographic exposures, when the first cropped image frame and a sequentially next image frame are aligned to create partial overlap in the images, the selected sequentially first portion of step 241 may comprise a non-overlapped part of the first cropped image frame plus half of the overlapping region.

Still referring to FIG. 3B, method 240 may further comprise measuring a displacement between each pair of sequentially adjacent cropped image frames 242 with respect to a longitudinal axis of the anatomical part being imaged. For clarity, the measuring step 242 could include measuring a displacement with respect to a longitudinal axis of the anatomical part being imaged between every pair of adjacent cropped image frames generated by a C-arm and received in step 210. Alternatively, measuring step 242 could occur after a step of selecting all of the constituent cropped image frames to be used to create a composite image, in which case only a displacement with respect to a longitudinal axis of the anatomical part being imaged between adjacent selected sequential cropped image frames that will be used to create the composite image will be measured. In an embodiment, measuring step 242 may include applying intensity-based image registration using a gradient descent algorithm. In an embodiment, measuring step 242 may measure a displacement between two cropped image frames with respect to a longitudinal axis of the anatomical part being imaged, an axis orthogonal to the longitudinal axis of the anatomical part being imaged, and/or a rotational axis about the anatomical part being imaged. Method 240 may further comprise selecting a plurality of interior portions from a plurality of cropped image frames occurring sequentially later than the first cropped image frame such that each interior portion may have a dimension corresponding to a measured displacement of step 242 between (a) the cropped image frame from which the immediately preceding selected portion was taken and (b) the cropped image frame providing the selected interior portion 244. For clarity, the first selected interior portion may have a dimension corresponding to the measured displacement between the first cropped image frame and a sequentially second cropped image frame, and a second selected interior portion may have a dimension corresponding to the measured displacement between the sequentially second cropped image frame and a sequentially third cropped image frame. Each selected interior portion from step 244 may be selected from an interior part of the cropped image frame providing the selected interior portion, as there may be less distortion in the interior part of the image frame. Each selected interior portion from step 244, in a composite image, may be disposed in the interior part of the composite image, i.e., between the sequentially first portion from step 241 and a sequentially last portion. Each selected interior portion from step 244 may have a dimension corresponding to—and in an embodiment, equal to—a respective measured displacement from step 242. For example, if measuring step 242 measures a displacement between two cropped image frames with respect to a longitudinal axis of an anatomical part being imaged, a selected interior portion may have a width equal to the measured displacement between the two cropped image frames. In such a case, the length of the selected interior portion may have a height corresponding to the height of the sequentially later cropped image frame. A composite image may have a plurality of selected interior portions, with each selected interior portion being selected from a respective cropped image frame from a sequence of cropped image frames. Method 240 may further comprise selecting a sequentially last portion from a last cropped image frame 245. The selected sequentially last portion of step 245 may correspond to an edge part of a composite image. In an embodiment, the selected sequentially last portion of step 245 may comprise up to about half of the last cropped image frame.

Figure 4A:
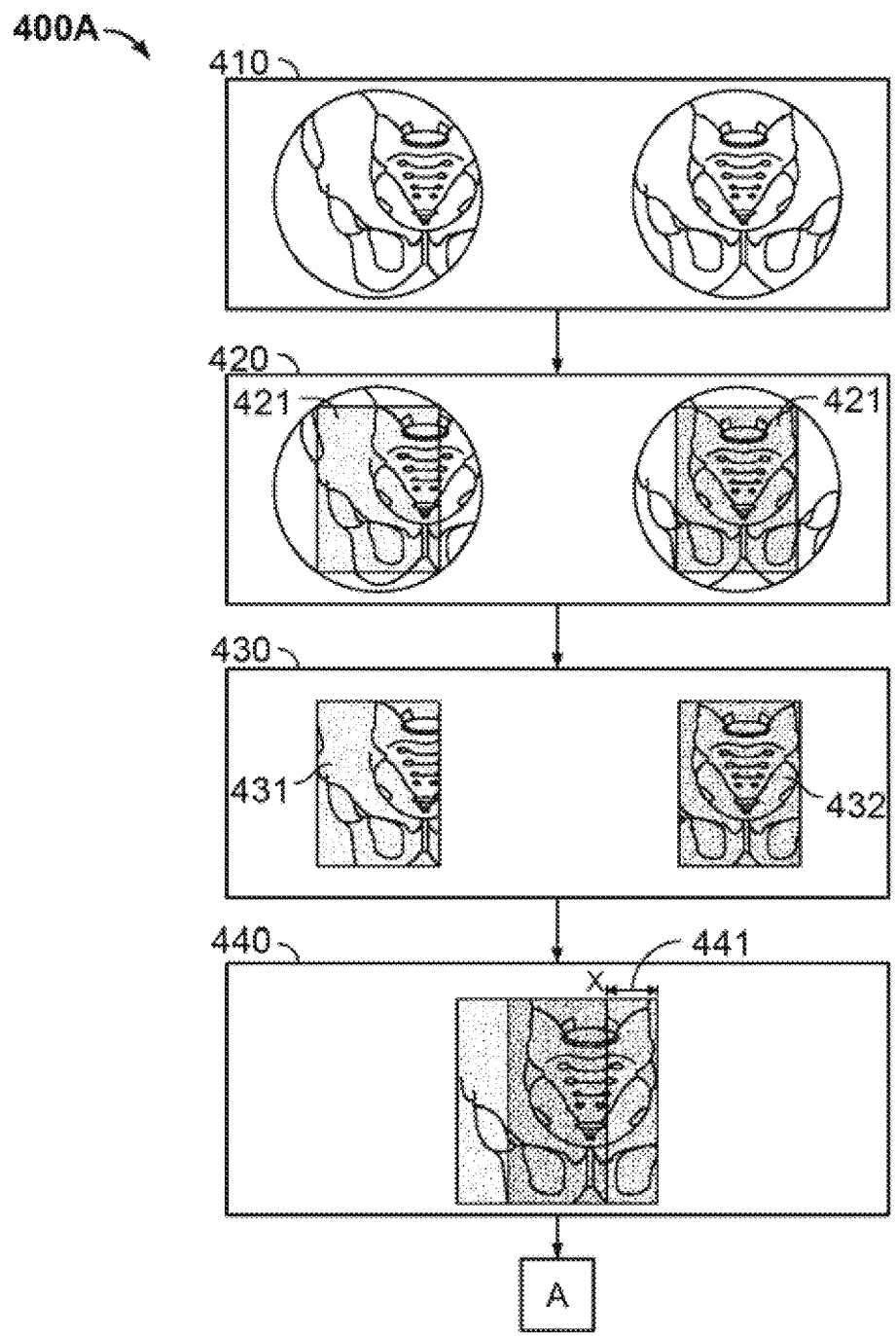
FIG. 4A depicts a first portion of an exemplary method for generating a composite radiographic image that corrects effects of parallax distortion in accordance with an aspect of the present disclosure.

FIG. 4A depicts a first part 400B of an exemplary method for generating a composite radiographic image that corrects effects of parallax distortion. Method 400A may comprise receiving a plurality of radiographic image frames pertaining to a patient 410. As an example, block 410 depicts two anteroposterior radiographic image frames of a patient's pelvis taken from a C-arm apparatus as the X-ray source and X-ray detector were rotated relative to the patient. Method 400A may further comprise identifying a region of interest 421 on the image frames 420. The region of interest 421 on each frame in block 420 is signified with shading.

Method 400A may further comprise cropping the identified region of interest 421 from a plurality of image frames 430 to generate cropped image frames 431, 432. In the example shown in block 430, cropped image frames 431, 432 are in a sequential order, with cropped image frame 431 being sequentially first and cropped image frame 432 being sequentially later relative to cropped image frame 431. Method 400A may further comprise measuring a displacement between each pair of sequentially adjacent cropped image frames 440 with respect to a longitudinal axis of the anatomical part being imaged. The displacement 441 between the cropped image frames 431, 432 in block 440, which have been aligned with respect to one another, can be seen. In an embodiment, measuring step 440 may include applying intensity-based image registration using a gradient descent algorithm. In an embodiment, measuring step 440 may measure a displacement between two cropped image frames with respect to a longitudinal axis of the anatomical part being imaged, an axis orthogonal to the longitudinal axis of the anatomical part being imaged, and/or a rotational axis about the anatomical part being imaged.

FIG. 4B depicts a second part 400B of the method from FIG. 4A. Method 400B may further include selecting an interior portion 450 from the sequentially later cropped image frame 432, the selected interior portion 452 having a dimension equal to the measured displacement 441 between cropped image frames 431, 432. The selected interior portion 452 can be seen as a shaded region 452 in the sequentially later cropped image frame 432. In an embodiment, the selected interior portion 452 may be taken from the interior 25% of the sequentially later cropped image frame 432 from an axis orthogonal to the longitudinal axis of the anatomical part being imaged. For example, in block 450, the longitudinal axis of the anatomical part being imaged extends from left to right in the drawings. Selected interior portion 452 can be seen as being taken from the axis orthogonal to the longitudinal axis of the anatomical part being imaged. A sequentially first portion 451 from a sequentially first cropped image frame 431 can also be seen as a shaded region 451. Method 400B may further comprise stitching 460 selected interior portion 452 to the first portion 451 to generate a partial composite image 461.

The series of steps may be repeated to select the sequentially next interior portion. FIG. 4C describes an exemplary next iteration. For example, referring back to block 420, the method may repeat the step of selecting a region of interest 421 from the next sequential pair of image frames; in this case, the pair of image frames would be the image frame from which cropped image frame 432 was generated and the sequentially next image frame occurring after image frame 432. The pair of image frames may be cropped as was done in block 430. A displacement 441 between cropped image frame 432 and the sequentially next cropped image frame 433 may be measured with respect to a longitudinal axis of the anatomical part being imaged as was done in block 440. A sequentially next interior portion 453 may be selected from cropped image frame 433. The selected interior portion 453 may have a dimension equal to the measured displacement 441 between cropped image frames 432, 433. The selected interior portion 453 may be taken from the interior 25% of cropped image frame 433. The selected interior portion 453 may be aligned and stitched to partial composite image 461.

Method 400B may include an iterative process 470 to select and add additional portions to the partial composite image, as described above, until the entire region of interest is entirely visible in the composite image. For example, if steps 420 through 460 were executed on a pair of image frames 1 and 2 from the set of image frames {1, 2, 3, 4, 5}, steps 420 through 460 would then be executed on image frames 2 and 3, again on image frames 3 and 4, and again until the composite image is entirely generated. As a result of method 400A, 400B, a composite image 481 is obtained at 480. Composite image 481 may correct effects of parallax distortion.

As described above, in an embodiment, measuring step 440 may include applying intensity-based image registration. Intensity-based image registration may be an iterative process that may include spatially registering a moving, or sequentially later, image frame with a reference, or sequentially earlier, image frame. Intensity-based image registration may involve comparing intensity patterns in images via correlation metrics, which may also be referred to as optimizers. The correlation metric or optimizer may define an image similarity metric for evaluating accuracy of a registration. The image similarity metric may take two images and return a scalar value describing the level of similarity between the images, and the optimizer may define the methodology for minimizing or maximizing the similarity metric.

Figure 11:
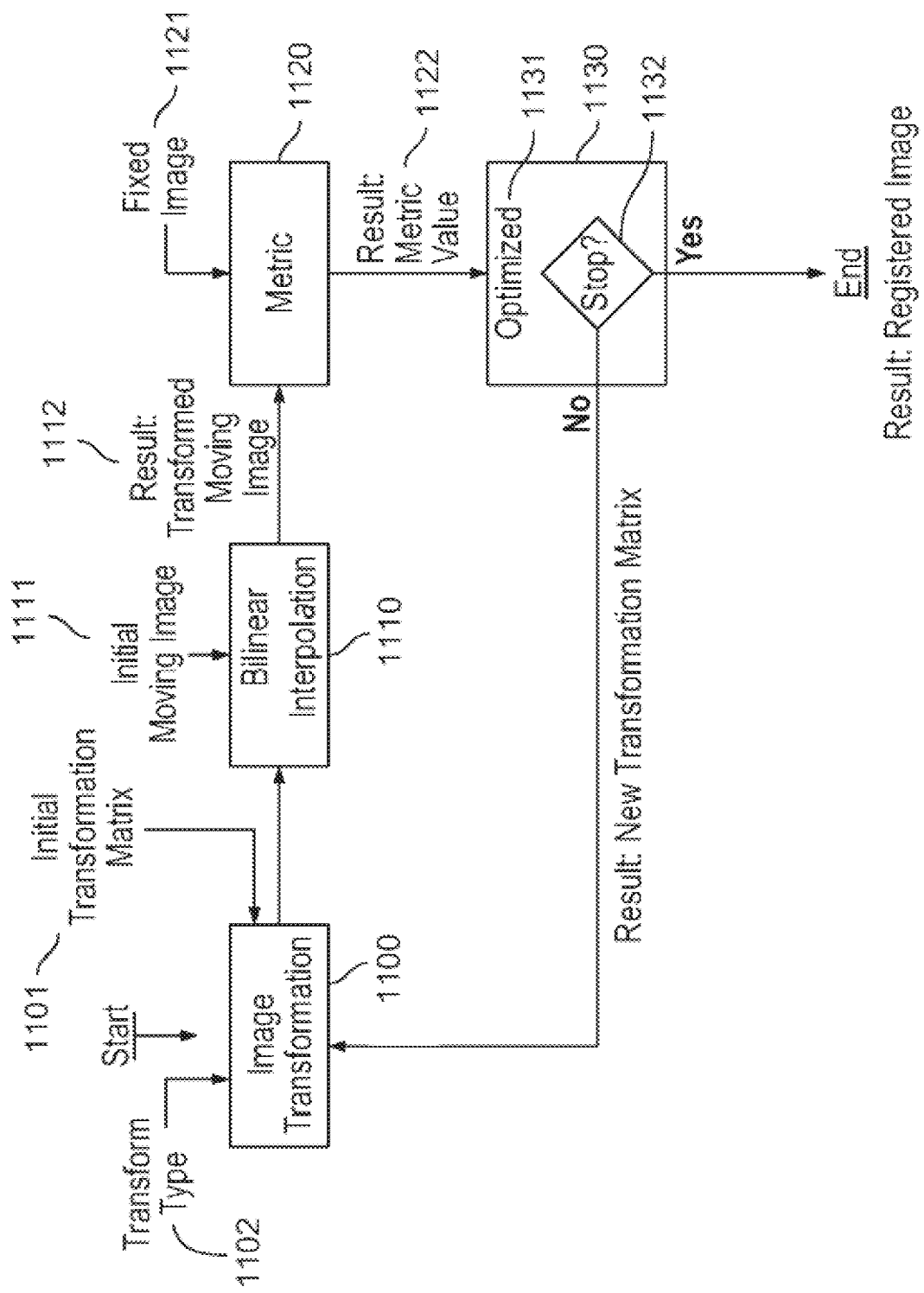
FIG. 11 shows a flow chart depicting an exemplary process of implementing intensity-based image registration in accordance with an aspect of the present disclosure.

FIG. 11 shows an exemplary flow chart describing an intensity-based image registration step. The process may begin at 1100 with an image transformation beginning with a pre-determined transformation matrix 1101 and a type of transformation 1102. A transformation may be applied to a moving image 1111 with bilinear interpolation at step 1110. At 1120 a metric may compare the transformed moving image 1112 to a fixed image 1121 to compute a metric value 1122. At 1130, an optimizer 1131 may check the metric value 1122 to determine if a terminating condition 1132 has been satisfied. If the terminating condition 1132 is not satisfied, the process will be repeated with a new transformation matrix generated with a gradient descent method until a defined number of iterations and/or a terminating condition 1132 is reached.

When building a composite image, the constituent portions must be properly aligned and stitched together. Edge detection software, such as software on Pro Imaging with Surgeon's Checklist offered by Radlink, may locate critical landmarks between the constituent portions and use the landmarks to properly align the constituent portions. The landmarks may be physically placed externally to the anatomical part being imaged within the image field of view, or the landmarks may comprise anatomical landmarks within the body. In this manner, selected portions may be aligned into true mathematical orientation with respect to one another. Once properly aligned, the constituent portions may be stitched together.

Figure 12:
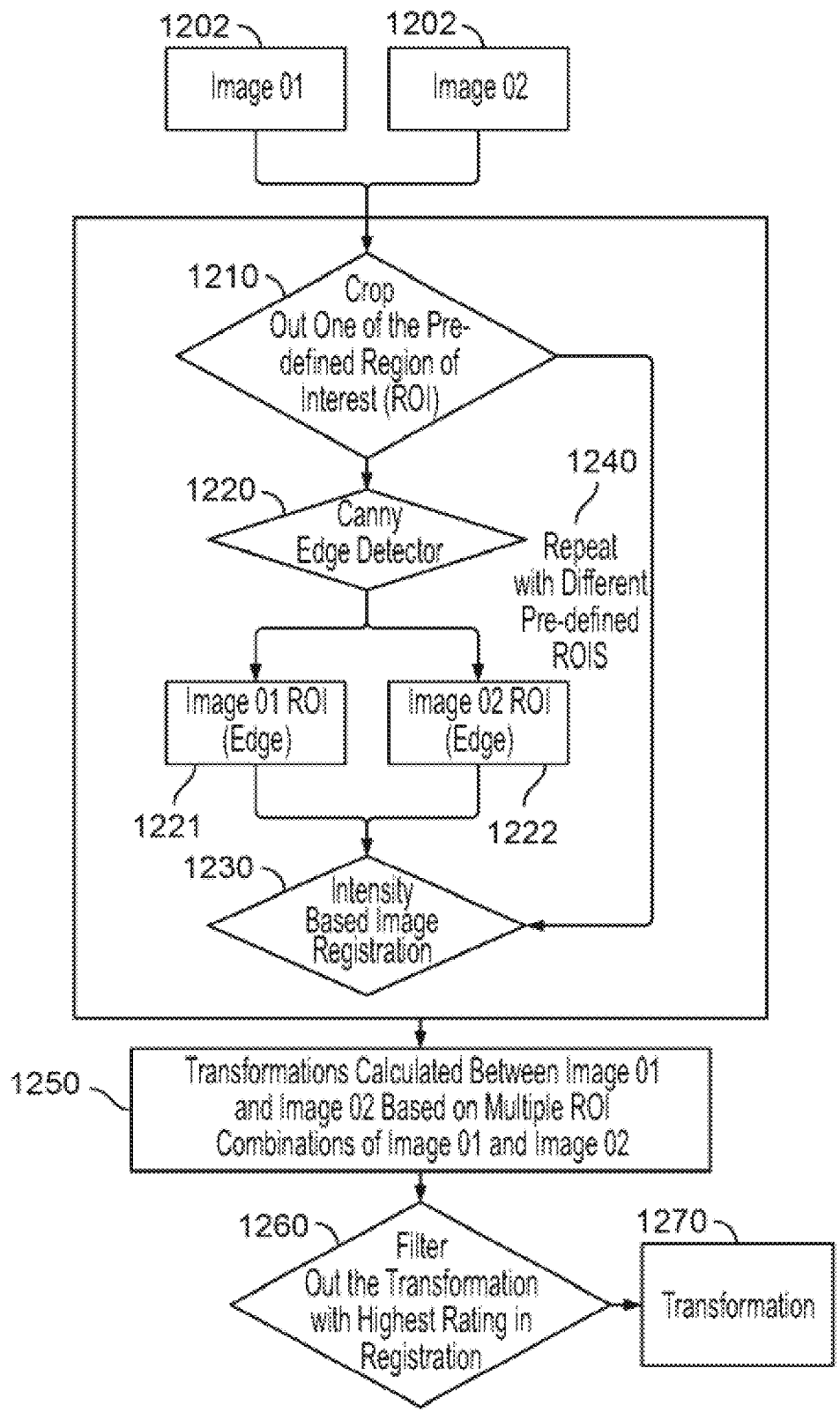
FIG. 12 shows an exemplary process that may be used in connection with measuring a displacement between two image frames generated from a plurality of discrete exposures according to an aspect of the present disclosure.

FIG. 12 illustrates an exemplary process for implementing at least a part of measuring step 440 in an embodiment where the radiographic images are generated from several discrete exposures. Reference image frame 1201 and moving image frame 1202 may be provided, and one of several pre-defined regions of interest may be cropped from image frames 1201, 1202 at step 1210. The cropped image frames from step 1210 may undergo a Canny edge detector process at 1220 to detect reference frame region of interest edges 1221 and moving frame region of interest edges 1222. Edges 1221, 1222 may undergo an intensity-based image registration progress, for example, as described in FIG. 11, at step 1230. At step 1240, reference image frame 1201 and moving image frame 1202 may undergo the same repeated process with a different, pre-defined region of interest cropped from image frames 1201, 1202. At step 1250, transformations may be calculated between reference image frame 1201 and moving image frame 1202 based on multiple region of interest combinations. At step 1260, the transformation with the highest metric value may be filtered to result in a transformed image 1270.

A Canny edge detector process, such as in the exemplary process described above, may include the following steps: (1) apply a Gaussian filter to smooth the image in order to remove noise; (2) find the intensity gradients of the image; (3) apply non-maximum suppression to get rid of spurious responses to edge detection; (4) apply double threshold to determine potential edges; and (5) track by hysteresis to finalize the detection of edges by suppressing all the other edges that are weak and not connected to strong edges.

Using one of the exemplary methods described above, two-dimensional composite radiographic imaging information that corrects effects of parallax distortion may be generated. An image displaying a wide field of view and that corrects effects of parallax distortion is a useful improvement in intra-operative imaging techniques and may allow members of a surgical team to make more accurate measurements during a procedure, resulting in improved outcomes for patients and more efficient surgical procedures.

Figure 5:
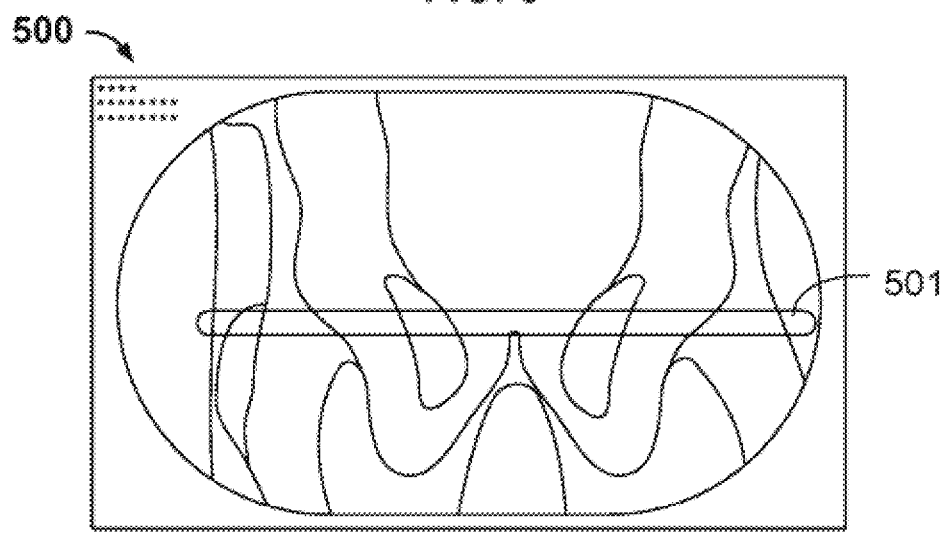
FIG. 5 shows a composite radiographic image that corrects effects of parallax distortion in accordance with an aspect of the present disclosure.

FIG. 5 shows a composite radiographic image that corrects effects of parallax distortion that was generated according to a method of the present disclosure. Composite image 500 depicts an anteroposterior image of a patient's pelvic region. Straight metal bar 501 is accurately depicted in composite image 500—straight, and without any visible curves or defects caused by parallax distortion. Composite image 500 was generated from a plurality of discrete radiographic exposures taken on a C-arm apparatus.

Figure 6:
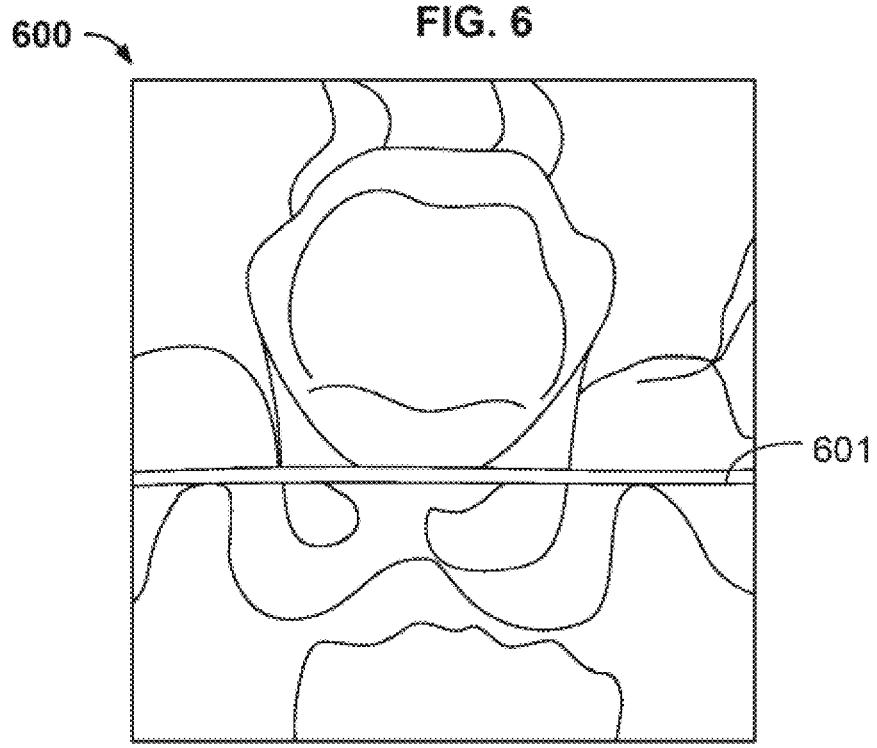
FIG. 6 shows a composite radiographic image that corrects effects of parallax distortion in accordance with an aspect of the present disclosure.

FIG. 6 shows a composite radiographic image that corrects effects of parallax distortion that was generated according to a method of the present disclosure. Composite image 600 depicts an anteroposterior image of a patient's pelvis. Straight metal bar 601 is accurately depicted in composite image 600—straight, and without any visible curves or defects caused by parallax distortion. Composite image 600 was generated from a plurality of radiographic image frames from a fluoroscopic procedure using a C-arm apparatus.

Figure 7:
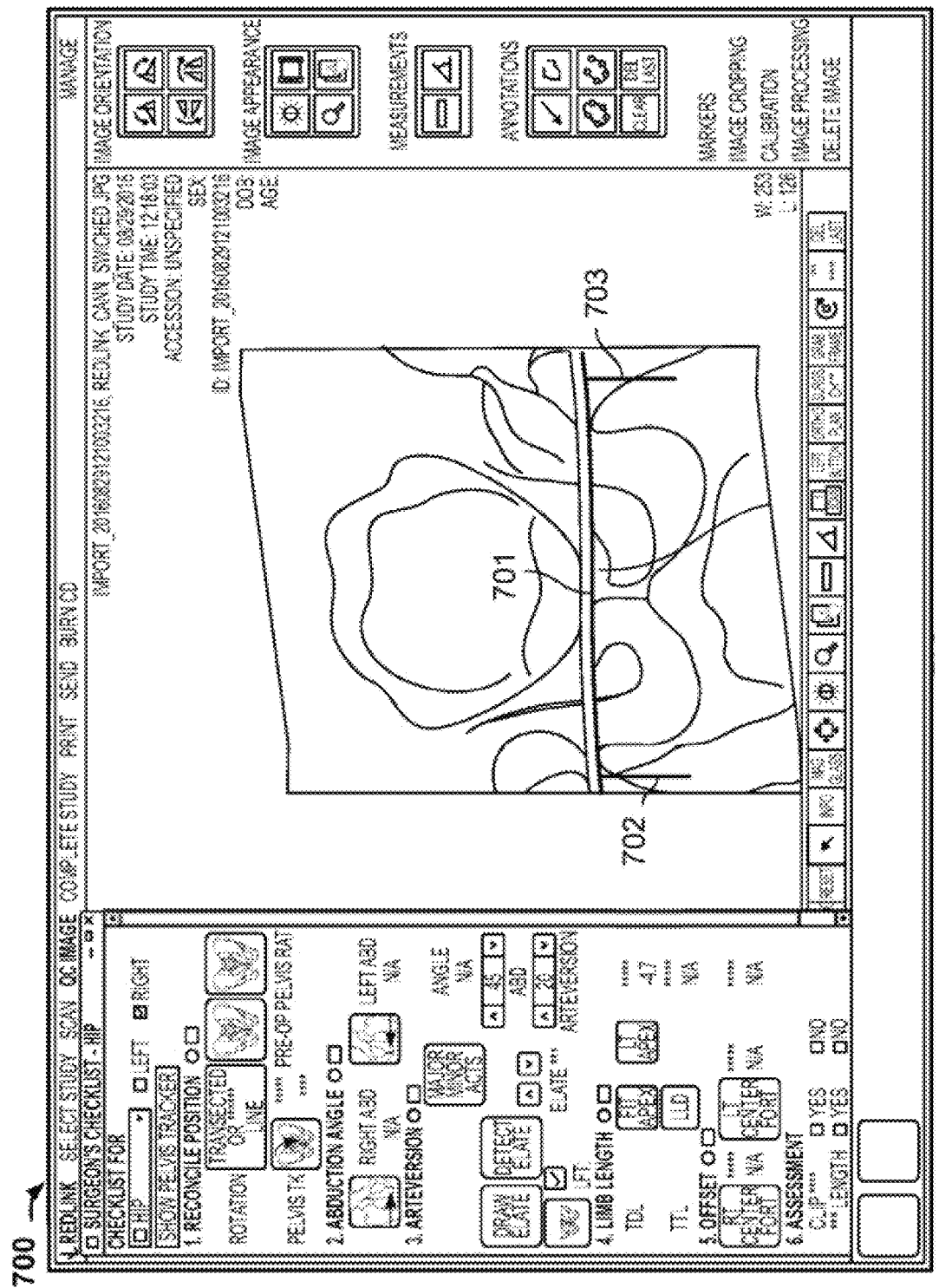
FIG. 7 depicts a composite anteroposterior radiographic image of a pelvis that corrects effects of parallax distortion being used to measure a discrepancy in leg lengths of a patient in accordance with an aspect of the present disclosure.

FIG. 7 depicts a composite anteroposterior radiographic image of a pelvis 700 that corrects effects of parallax distortion. Because composite image 700 corrects effects of parallax distortion, it can be used intra-operatively to accurately make measurements, such as a discrepancy in leg lengths 702, 703. Straight metal bar 701 can be seen accurately depicted in composite image 700. Composite image 700 was generated from a plurality of radiographic image frames from a fluoroscopic procedure using a C-arm apparatus.

Figure 8:
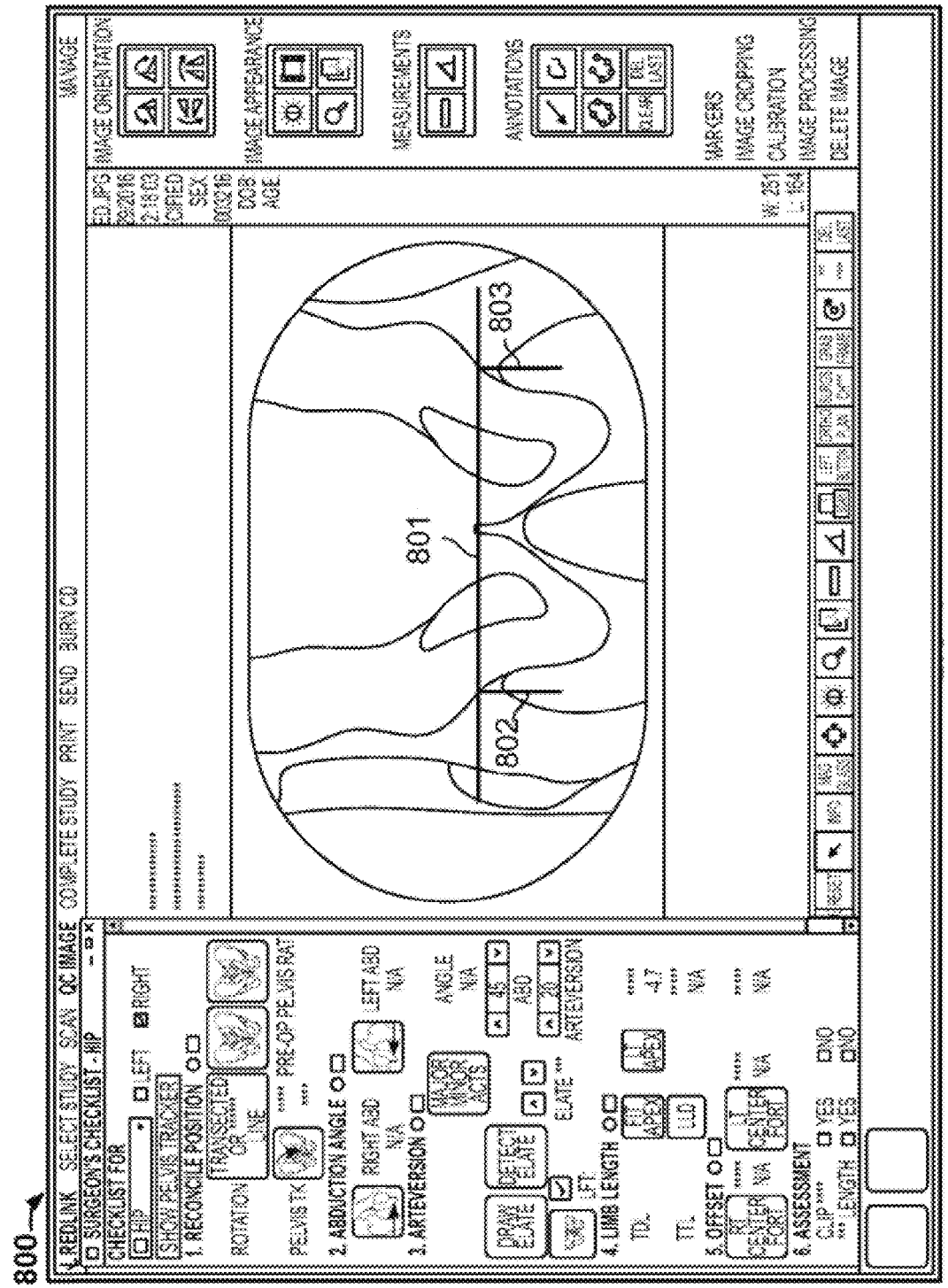
FIG. 8 depicts a composite anteroposterior radiographic image of a pelvis that corrects effects of parallax distortion being used to measure a discrepancy in leg lengths of a patient in accordance with an aspect of the present disclosure.

FIG. 8 depicts a composite anteroposterior radiographic image of a pelvis 800 that corrects effects of parallax distortion. Because composite image 800 corrects effects of parallax distortion, it can be used intra-operatively to accurately make measurements, such as a discrepancy in leg lengths 802, 803. Straight metal bar 801 can be seen accurately depicted in composite image 800. Composite image 800 was generated from a plurality of discrete radiographic exposures taken on a C-arm apparatus.

Figure 10:
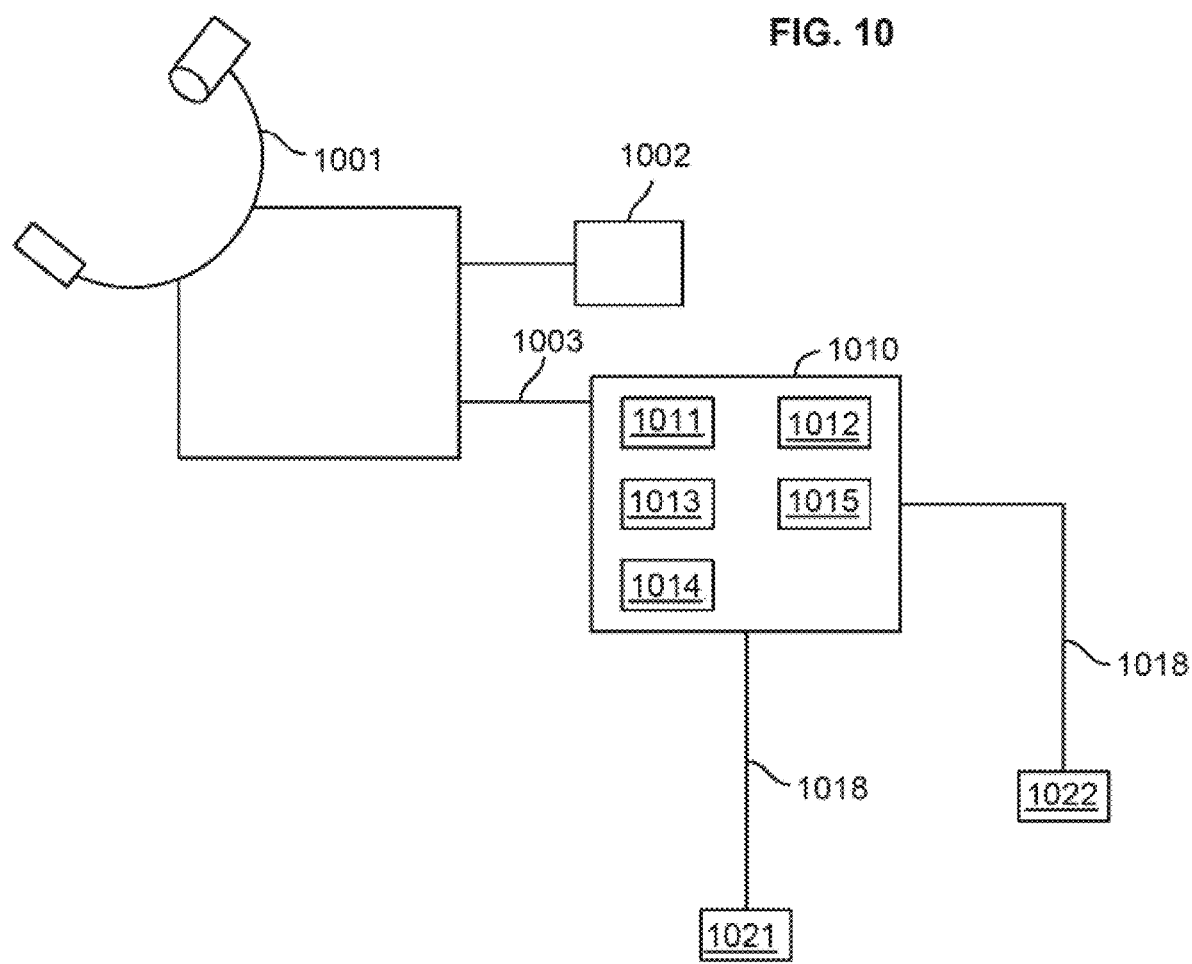
FIG. 10 depicts a block diagram of an exemplary environment that may be used to implement systems and methods of the present disclosure.

The methods and systems described in the present disclosure may be implemented using certain hardware. For example, referring to FIG. 10, a C-arm apparatus 1001 may capture video or image signals. The C-arm apparatus 1001 may have a display 1002 directly connected to the apparatus to instantly view the images or video. A wireless kit 1010 may, alternatively or additionally, be attached to the C-arm apparatus 1001 via video port 1003 to receive the video or image signal from the C-arm apparatus 1001, the intra-operative signal representing digital data of a radiographic image frame or plurality of frames. Video port 1003 may utilize a BNC connection, a VGA connection, a DVI-D connection, or an alternative connection known to those of skill in the art. Unique in the field in its ability to convert any wired image acquisition device (such as a C-arm) into a wireless imaging device, the wireless kit 1010 may be the Radlink Wireless C-Arm Kit. Wireless kit 1010 may include a resolution converter 1011 to convert the image signal to proper resolution for further transmission, frame grabber 1012 to produce a pixel-by-pixel digital copy of each image frame, central processing unit 1013, memory 1014, and dual-band wireless-N adapter 1015. The wireless kit 1010 may convert the received signal to one or more image files and can send the converted file(s), for example, by wireless connection 1018 to one or more computer(s) and operatively connected display(s) 1021, 1022.

The computer and operatively connected display may, for example, be a Radlink Galileo Positioning System ("GPS") 1021 or GPS Tablet 1022. The Wireless C-Arm Kit 1010 may receive, convert, and transmit the file(s) in real time. The methods described in the present disclosure may be implemented, for example, as software running on the GPS 1021 or GPS Tablet 1022 units. The GPS 1021 and GPS Tablet 1022 may also incorporate additional functions, such as those provided in the Radlink Pro Imaging with Surgeon's Checklist software. Using such equipment, a composite image that corrects effects of parallax distortion may thus be generated and viewed intra-operatively in real time.

Figure 9:
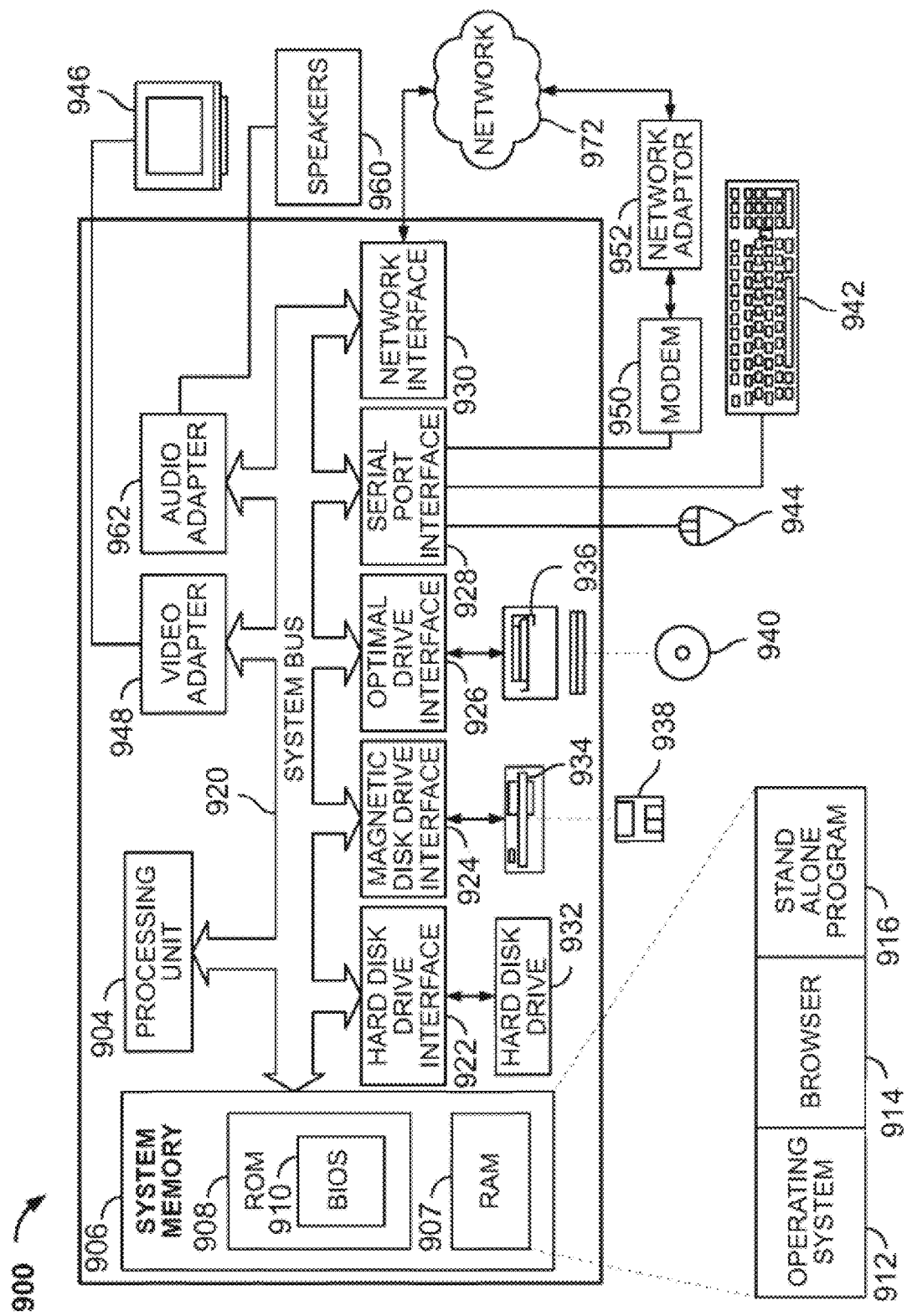
FIG. 9 shows an embodiment of a computer architecture according to the present disclosure.

FIG. 9 depicts exemplary hardware for a system to generate intra-operative composite radiographic imaging information that correct effects of parallax distortion to generate and utilize a three-dimensional patient model to determine a proper placement of a component during a surgery. The system, or part thereof, may take the form of a computer 900 that includes a processing unit 904, a system memory 906, and a system bus 920 that operatively couples various system components, including the system memory 906 to the processing unit 904. There may be only one or there may be more than one processing unit 904, such that the processor of computer 900 comprises a single central processing unit (CPU), or a plurality of processing units, commonly referred to as a parallel processing environment. The computer 900 may be a conventional computer, a distributed computer, a web server, a file server, a tablet or iPad, a smart phone, or any other type of computing device.

The system bus 920 may be any of several types of bus structures including a memory bus or memory controller, a peripheral bus, a switched fabric, point-to-point connections, and a local bus using any of a variety of bus architectures. The system memory 906 may also be referred to as simply the memory, and includes read only memory (ROM) 908 and random access memory (RAM) 907. A basic input/output system (BIOS) 910, containing the basic routines that help to transfer information between elements within the computer 900, such as during start-up, is stored in ROM 908. The computer 900 may further include a hard disk drive 932 for reading from and writing to a hard disk, not shown, a magnetic disk drive 934 for reading from or writing to a removable magnetic disk 938, and/or an optical disk drive 936 for reading from or writing to a removable optical disk 940 such as a CD-ROM or other optical media.

The hard disk drive 932, magnetic disk drive 934, and optical disk drive 936 may be connected to the system bus 920 by a hard disk drive interface 922, a magnetic disk drive interface 924, and an optical disk drive interface 926, respectively. The drives and their associated computer-readable media provide nonvolatile storage of computer-readable instructions; data structures, e.g., a catalog and a context-based index; program modules, e.g., a web service and an indexing robot; and other data for the computer 900. It should be appreciated by those skilled in the art that any type of computer-readable media that can store data that is accessible by a computer, for example, magnetic cassettes, flash memory cards, USB drives, digital video disks, RAM, and ROM, may be used in the exemplary operating environment.

A number of program modules may be stored on the hard disk 932, magnetic disk 934, optical disk 936, ROM 908, or RAM 907, including an operating system 912, browser 914, stand-alone program 916, etc. A user may enter commands and information into the personal computer 900 through input devices such as a keyboard 942 and a pointing device 944, for example, a mouse. Other input devices (not shown) may include, for example, a microphone, a joystick, a game pad, a tablet, a touch screen device, a satellite dish, a scanner, a facsimile machine, and a video camera. These and other input devices are often connected to the processing unit 904 through a serial port interface 928 that is coupled to the system bus 920, but may be connected by other interfaces, such as a parallel port, game port or a universal serial bus (USB).

A monitor 946 or other type of display device is also connected to the system bus 920 via an interface, such as a video adapter 948. In addition to the monitor 946, computers typically include other peripheral output devices, such as speakers 960 connected to the system bus 920 via an audio adapter 96 and printers. These and other output devices are often connected to the processing unit 904 through the serial port interface 928 that is coupled to the system bus 920, but may be connected by other interfaces, such as a parallel port, game port, or a universal serial bus (USB).

The computer 900 may operate in a networked environment using logical connections to one or more remote computers. These logical connections may be achieved by a communication device coupled to or integral with the computer 900; the application is not limited to a particular type of communications device. The remote computer may be another computer, a server, a router, a network personal computer, a client, a peer device, or other common network node, and typically includes many or all of the elements described above relative to the computer 900, although only a memory storage device has been illustrated in FIG. 9. The computer 900 can be logically connected to the Internet 972. The logical connection can include a local area network (LAN), wide area network (WAN), personal area network (PAN), campus area network (CAN), metropolitan area network (MAN), or global area network (GAN). Such networking environments are commonplace in office networks, enterprise-wide computer networks, intranets and the Internet, which are all types of networks.

When used in a LAN environment, the computer 900 may be connected to the local network through a network interface or adapter 930, which is one type of communications device. When used in a WAN environment, the computer 900 typically includes a modem 950, a network adapter 952, or any other type of communications device for establishing communications over the wide area network. The modem 950, which may be internal or external, is connected to the system bus 920 via the serial port interface 928. In a networked environment, program modules depicted relative to the personal computer 900, or portions thereof, may be stored in a remote memory storage device. It is appreciated that the network connections shown are exemplary and other means of, and communications devices for, establishing a communications link between the computers may be used.

The system can take the form of a computer program product 916 accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connectionwith the instruction execution system, apparatus, or device.

The medium can be an apparatus or device that utilizes or implements electronic, magnetic, optical, electromagnetic, infrared signal or other propagation medium, or semiconductor system. Examples of a computer-readable medium comprise a semiconductor or solid-state memory, magnetic tape, a removable computer diskette, a random access memory, a read-only memory, a rigid magnetic disk and an optical disk. Current examples of optical disks comprise compact disk-read only memory (CD-ROM), compact disk-read/write (CD-R/W) and DVD formats.

A data processing system suitable for storing and/or executing program code comprises at least one processor coupled directly or indirectly to memory elements through a system bus. The memory elements can include local memory employed during actual execution of the program code, bulk storage, and cache memory that provide temporary storage of at least some program code in order to reduce the number of times code is retrieved from bulk storage during execution.

Input/output or I/O devices (including, but not limited to, keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modems and Ethernet cards are just a few of the currently available types of network adapters.

Furthermore, computers and other related electronic devices can be remotely connected to either the LANs or the WAN via a digital communications device, modem and temporary telephone, or a wireless link. It will be appreciated that the Internet comprises a vast number of such interconnected networks, computers, and routers.

Figure 13:
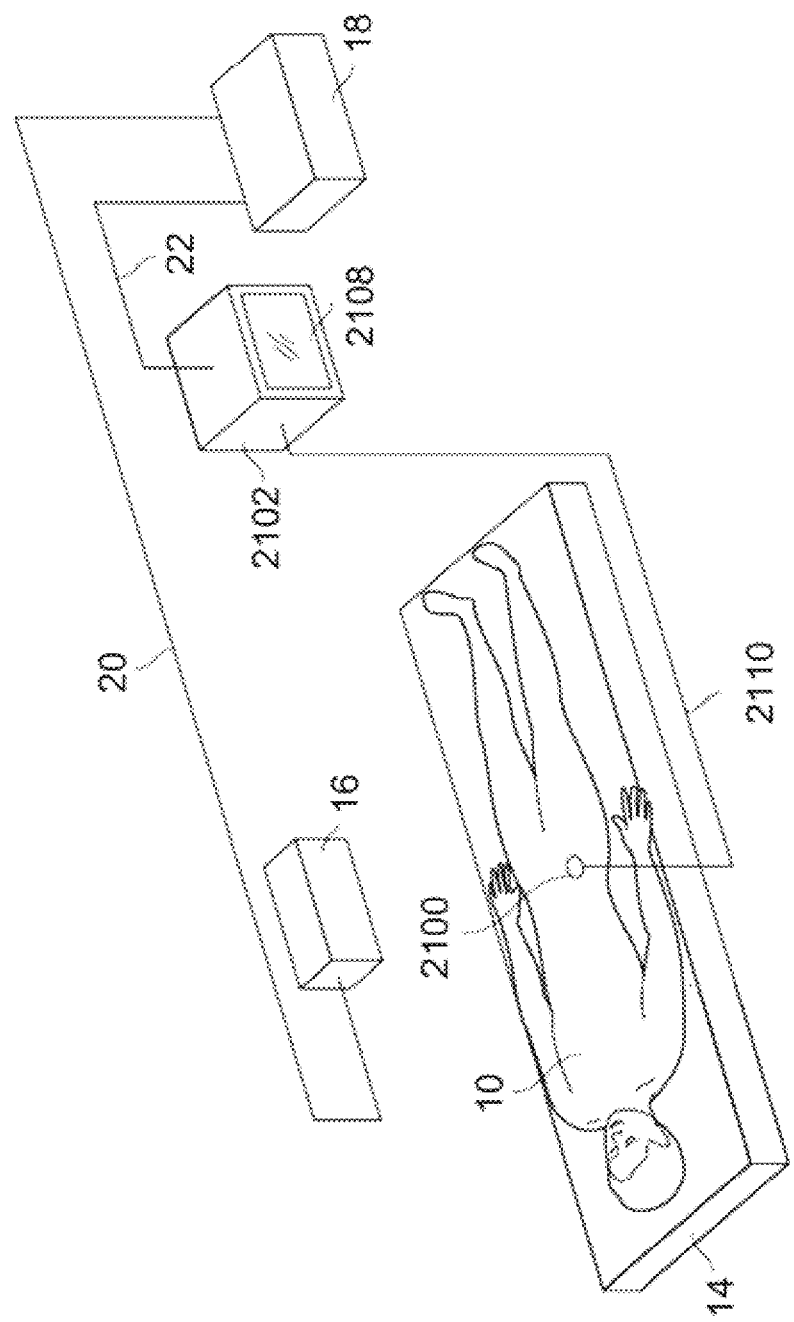
FIG. 13 is a block diagram view of an exemplary system and an associated patient and x-ray shows an embodiment of exemplary system architecture in accordance with an embodiment of the present disclosure.

Referring to FIG. 13, a computerized surgery assist computer 2102 may receive anatomic image information of a patient 10 or a portion of a patient 10 (e.g., a pelvis) taken by an anatomical scanning device, such as an x-ray scanner 16 (e.g., when receiving discrete images or fluorographic images) at a position of the patient 10 (lying on a patient table 14).

Alternatively, the computerized surgery assist computer 2102 may receive anatomic image information of a patient 10 or a portion of a patient 10 obtained from a CT or MR scan. For example, in such an embodiment, the anatomic image information may be a data set of three-dimensional imaging information. In an embodiment, the computerized surgery assist computer 2102 may receive a data set of three-dimensional imaging information obtained while the patient 10 was in a neutral position. The anatomic image information may be received from an image processing computer server 18 positioned via wired or wireless data links 20, 22 between the x-ray scanner 16 (or, e.g., the CT or MR scanner) and the surgery assist computer 2102.

Optionally, the patient may have a three-dimensional positional sensor 2100 affixed to the patient's body, and the surgery assist computer 2102 may receive positional information via wired or wireless data link 2110 from sensor 2100. The surgery assist computer 2102 may be programmed to display a visual representation of the anatomic image information on a computerized display 2108; determine a target positioning value of a component from the anatomic image information, either automatically or with input from a surgeon; and may make additional measurements as desired or programmed (e.g., measurements of one or more anatomical landmarks and/or ratios of anatomical landmarks), either automatically or with input from a surgeon.

The surgery assist computer 2102 may further receive subsequent anatomic image information of the patient 10; display a visual representation of the subsequent anatomic image information on the display 2108; and may make additional measurements or display additional markers, either automatically or with input from a surgeon.

The surgery assist computer 2102 may have a receiver to receive information and data, including image data from the x-ray scanner 16 and/or CT or MR scanner; a processor or microcontroller, such as a CPU, to process the received information and data and to execute other software instructions; system memory to store the received information and data, software instructions, and the like; and a display 2108 to display visual representations of received information and data as well as visual representations resulting from other executed system processes.

Figure 14C:
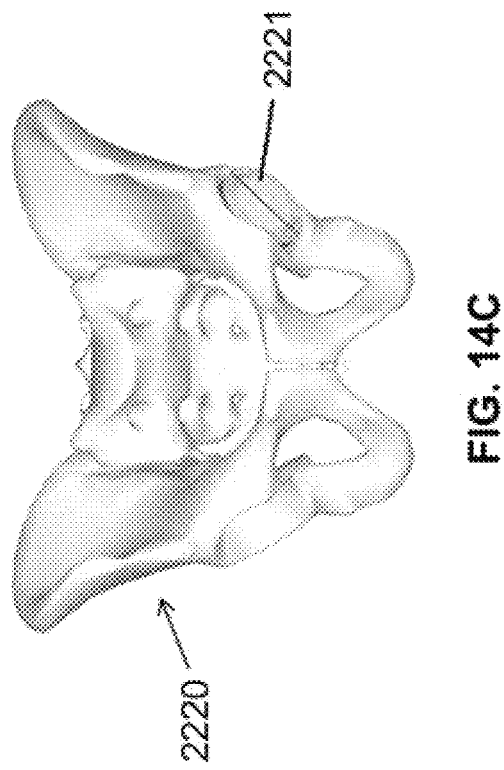
FIG. 14C shows a portion of a patient at a non-neutral position with backward tilt.
Figure 14A:
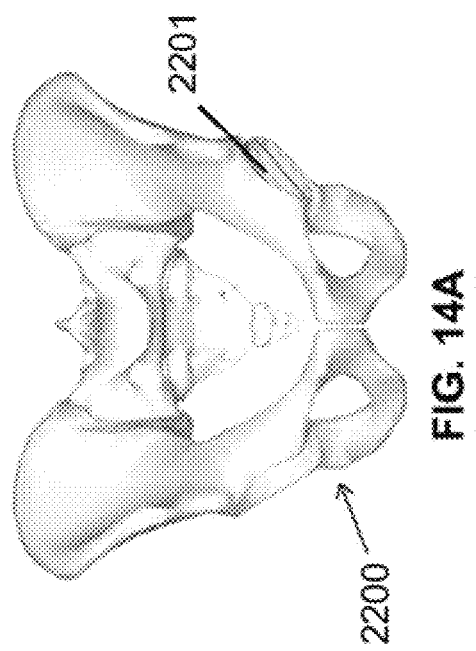
FIG. 14A shows a portion of a patient at a neutral position with no tilt.
Figure 14B:
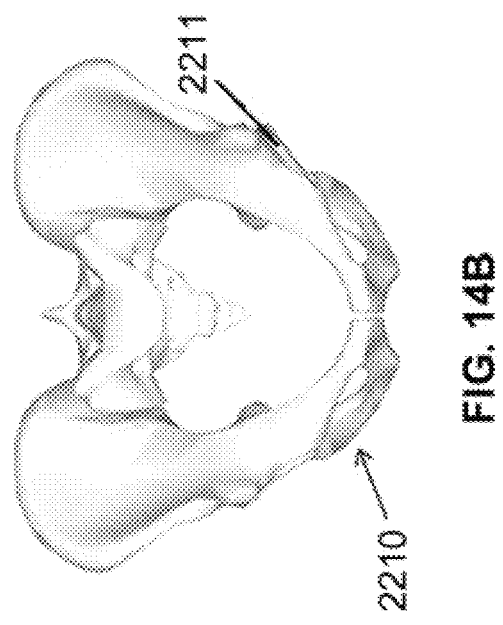
FIG. 14B shows a portion of a patient at a non-neutral position with forward tilt.

Such a system may allow a surgeon and/or other medical personnel to more accurately and consistently determine a proper placement of and position a component by helping a surgeon identify a target position for a component and making adjustments to the positioning value based on differences in initial anatomic image information and subsequent anatomic image information. Such differences may result, for example, when a patient and an imaging scanner are aligned differently with respect to each other when multiple sets of anatomic image information are acquired (e.g., pre-operatively at a neutral position of a patient and intra-operatively at a non-neutral position of the patient). FIGS. 14A-14C provide examples of a portion of a patient 2200 (in this case, the patient's pelvis) may appear differently when a patient is positioned in different orientations. For example, FIG. 14A shows a portion of the patient 2200 in a neutral position with no tilt, while FIG. 14B shows a portion of the patient 2210 with a forward tilt of about 20°, and FIG. 14C shows a portion of the patient 2220 having a backward tilt of about −20°. Of course, moving a patient may also cause the portion of the patient to have different inclinations and anteversions, as a patient is generally manipulated in three-dimensional space. Importantly, small differences in a patient's orientation relative to a neutral position may provide different measurements of anatomical or component orientations, which could affect the outcome of a surgical procedure. For example, an acetabular cup 2201 is positioned with an inclination of 40.0° and an anteversion of 20.0°. If pelvis 200 is tilted 20.0°, as pelvis 210 is in FIG. 14B, the acetabular cup 2211 is measured to have an inclination of 37.3° and an anteversion of 4.3°. If pelvis 200 is tilted to −20.0°, as is pelvis 220 in FIG. 14C, the acetabular cup 2221 is measured to have an inclination of 47.2° and an anteversion of 34.6°. Accordingly, when positioning a component in a patient during surgery, such as an acetabular cup during THA, a surgeon may need to account for the effects of the patient's orientation on positioning values such as tilt, inclination, and/or anteversion.

Figure 17:
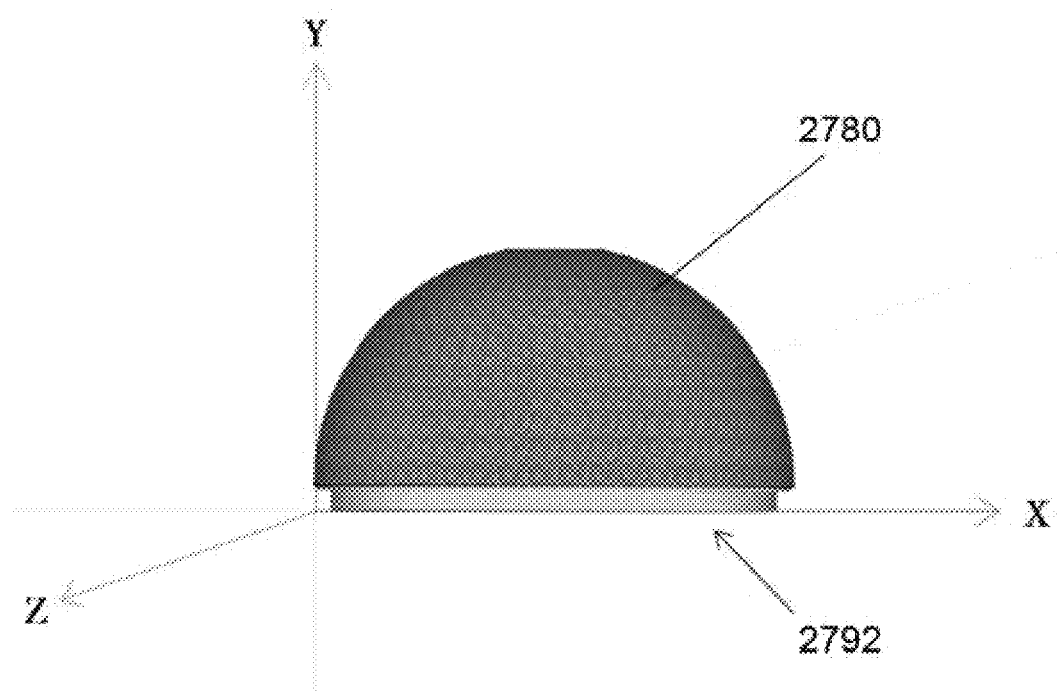
FIG. 17 shows a projected circle rotated along three axes that may be used to model an acetabular cup component in accordance with an embodiment of the present disclosure.
Figure 18:
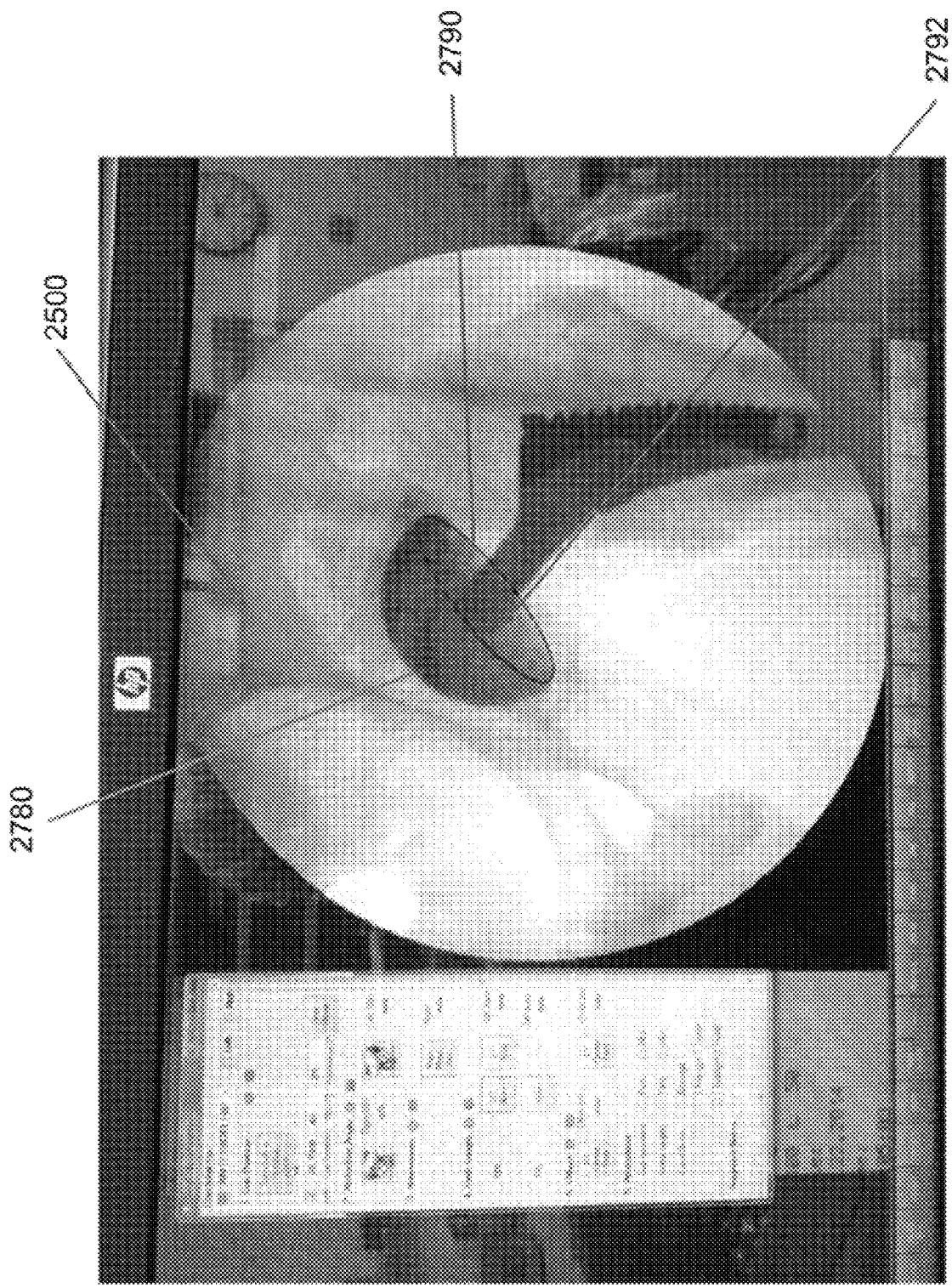
FIG. 18 shows a screen shot of a display including an intra-operative radiographic image including a superimposed ellipse representing a target placement of an acetabular cup component in accordance with an embodiment of the present disclosure.

Adjustments to positional values of the acetabular cup, such as inclination, may be based on the study of a projected circle in three-dimensional space. The rotation of the circle in three-dimensional space may mimic the rotation of an acetabular cup. An acetabular cup may display shapes of ellipses under different angles of projection. Three rotational factors may affect the shape of the projected ellipse: Inclination (I)—rotation about the Z axis, Anteversion (A)—rotation about the Y axis, and Tilt (T)—rotation about the X axis. FIG. 17 illustrates an exemplary projection of a circle that may be used to model an opening 2792 of an acetabular cup 2780 with the X, Y, and Z axes labeled.

With reference to FIG. 17, the rotational matrices along the X, Y, and Z axes may be described as follows:

$$R_x(T) = \begin{bmatrix} 1 & 0 & 0 \\ 0 & \cos(T) & -\sin(T) \\ 0 & \sin(T) & \cos(T) \end{bmatrix}$$

$$R_y(A) = \begin{bmatrix} \cos(A) & 0 & \sin(A) \\ 0 & 1 & 0 \\ -\sin(A) & 0 & \cos(A) \end{bmatrix}$$

$$R_Z(I) = \begin{bmatrix} \cos(I) & -\sin(I) & 0 \\ \sin(I) & \cos(I) & 0 \\ 0 & 0 & 1 \end{bmatrix}$$

The following matrix may capture the initial circle lying on the X-Z plane:

$$\text{circle} = \begin{bmatrix} R*\sin(\theta) \\ 0 \\ R*\cos(\theta) \end{bmatrix}$$

The normal of the circle may be in the direction of the Y-axis and may be described as follows:

$$\text{Normal} = \begin{bmatrix} 0 \\ -1 \\ 0 \end{bmatrix}$$

After three rotations, the parametric equations of the circle projected on the X-Y plane may be described as follows:

$X=R*[\sin(\theta)*\cos(I)*\cos(A)+\cos(\theta)*\sin(A)]$; and $Y=R*\cos(T)*\sin(\theta)*\sin(I)-R*[-\sin(\theta)*\cos(I)*\sin(A)*\sin(T)+\cos(\theta)*\cos(A)*\sin(T)]$.

where X and Y represent the coordinates of the projected ellipse on the X-Y plane, R represents the size of the acetabular cup, and θ represents the parameter.

After three rotations along the three axes, the parametric equations of the normal of the circle surface may be described as follows:

$X_{normal}=\sin(I)*\cos(A)$ $Y_{normal}=-\cos(I)*\cos(T)+\sin(I)*\sin(A)*\sin(T)$ The normal of the circle has the property that it is always parallel to the minor diameter of the projected ellipse. Accordingly, the minor diameter of the projected ellipse may be derived and described as follows:

Minor Diameter=$\sin(a\,\cos(\sqrt{X_{normal}^2+Y_{normal}^2}))*2*R$

The major diameter may be described as follows:

Major Diameter=$2*R$

Accordingly, the inclination value of the projected ellipse may be described as follows:

$$\text{Projected Ellipse } Incl. = a\tan\left(\frac{X_{normal}}{Y_{normal}}\right)$$

Therefore, if an acetabular cup is placed or has target positioning values with a known inclination and anteversion, the inclination resulting after the acetabular cup is tilted (e.g., when the pelvis is tilted) may be calculated. Other positioning values may similarly be calculated, as will be apparent to one of ordinary skill in the art.

Unless otherwise expressly stated or obviously required by context, steps in methods described herein need not be performed in a particular order. Rather, an example order may be provided for ease of explanation.

In an embodiment, the surgery assist computer 2102 may be configured to implement one or more methods of the present disclosure. For example, with reference to FIG. 15, one method 2300 may be used to position a component intra-operatively. The example method 2300 may include a step 2310 of receiving a data set of imaging information representing at least a first portion of a patient (e.g., a data set of three-dimensional imaging information from a CT or MR scan) in a neutral position. Method 2300 may further include a step 2320 of generating a three-dimensional model of the first portion of the patient based on the data set of imaging information. The three-dimensional model may be reconstructed based on a region grow algorithm, water shed algorithm, active contour algorithm, a combination of algorithms, or any algorithm that may be known to those of ordinary skill in the art for generating a three-dimensional model from a data set of imaging information. Method 2300 may additionally include a step 2330 of iteratively rendering a plurality of two-dimensional projections from the three-dimensional model, each two-dimensional projection having a corresponding spatial orientation. The two-dimensional projections may be made at a specified orientation and distance (e.g., an x-ray-source-to-detector distance or an object-to-detector distance).

Alternatively, method 2300 may include a step 2330 of rendering a first two-dimensional projection from the three-dimensional model, the first two-dimensional projection having a corresponding spatial orientation, proceeding through step 2360 (described in example form below), then repeating step 2330 with a next sequential projection (or even an out of order projection).

Method 2300 may include a step 2340 of receiving intra-operative imaging information (e.g., an intra-operative x-ray image) representing the first portion of the patient. Method 2300 may further include a step 2350 of identifying a bony edge contour in the intra-operative imaging information. In an embodiment, the bony edge contour in the intra-operative imaging information may be detected using a canny edge detector algorithm, another edge-detection algorithm that may be known to those of ordinary skill in the art, a combination of algorithms, shape-based segmentation, or manual selection. In an embodiment, a canny edge detector process, such as in the exemplary process described above, may include the following steps: (1) apply a Gaussian filter to smooth the image in order to remove noise; (2) find the intensity gradients of the image; (3) apply non-maximum suppression to get rid of spurious responses to edge detection; (4) apply double threshold to determine potential edges; and (5) track by hysteresis to finalize the detection of edges by suppressing all the other edges that are weak and not connected to strong edges.

Method 2300 may further include the step 2360 of scoring each two-dimensional projection by calculating the distance of the bony edge contour in the intra-operative imaging information to a corresponding contour in each two-dimensional projection and identifying a global minimum score. Scoring step 2360 may be performed using best-fit techniques. In an alternate embodiment, such as when the system initially renders only a first two-dimensional projection before proceeding through the method, step 2360 may include scoring only the first two-dimensional projection, storing the score in memory, and repeating scoring step 2360 for subsequent two-dimensional projections as they are rendered, then selecting a global minimum score from the plurality of scores. A repetitive process such as this may be illustrated by steps 2330, 2360, and 2370 in FIG. 15. The process of repeating 2330, 2360, and 2370 may be referred to as an enumeration process 2380 based on the fitting of the two-dimensional projection and the detected bony edge contour from the intra-operative imaging information.

Method 2300 may include a step 2390 of outputting the orientation of the three-dimensional model as a final result. In an embodiment, step 2390 may include outputting a transformation matrix for the two-dimensional projection having the global minimum score, the transformation matrix representing the orientation of the three-dimensional model relative to the neutral position when the two-dimensional projection having the global minimum score was rendered.

Figure 16:
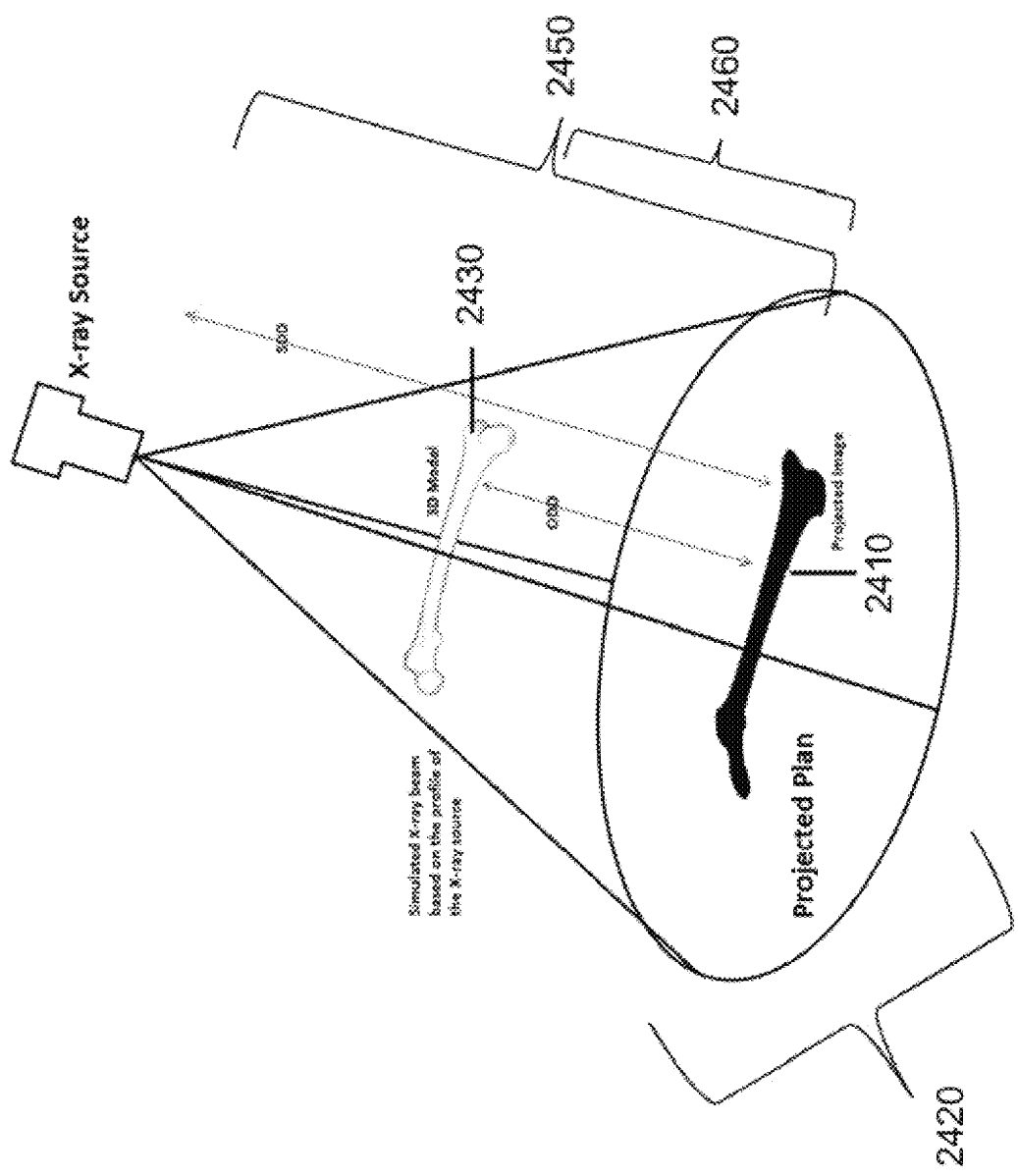
FIG. 16 is a diagram providing a conceptual model of a two-dimensional projection from a three-dimensional model in accordance with an embodiment of the present disclosure.

In an embodiment, a method may include a step of calculating an adjustment factor based on the transformation matrix. The calculated adjustment factor may be used to output a visual indication of an intra-operative adjustment to be made to a component based on the adjustment factor to achieve a target component orientation. For example, FIG. 16 illustrates one embodiment of such a visual indication 2790. Still referencing FIG. 16, for example, in a THA surgical procedure, an image of an ellipse 2790 may be superimposed onto radiographic image 2500 to illustrate how the opening 2792 of acetabular cup 2780 should appear when properly aligned. In an alternate embodiment, a method may include the step of applying the calculated adjustment factor to an intra-operative leg length measurement and outputting a visual indication of an intra-operative adjustment to be made to the patient to achieve a target leg length measurement. In an embodiment, the radiographic image 2500 (and any visual indication discussed in a similar context) may be displayed on display 2108 from FIG. 15. In an embodiment, a visual indication may include an outline of the target component orientation; real-time inclination, anteversion, and tilt values of the component; target inclination, anteversion, and tilt values of the component; and/or combinations thereof.

FIG. 16 illustrates a conceptual model of a two-dimensional projection 2410 from a three-dimensional model 2430 in accordance with an embodiment of the present disclosure. As discussed above, one or more two-dimensional projection(s) 2410 may be rendered based on the three-dimensional model 2430 onto a projected plan view 2420. Projected plan view 2420 may be comparable to an x-ray image, where the two-dimensional projection 2410 may be comparable to an anatomical visualization on an x-ray image. Each two-dimensional projection may have a corresponding spatial orientation depending on the position of the x-ray source 16a to the three-dimensional model 2430. Of course, FIG. 16 may represent a conceptualization of rendering two-dimensional projections, so there is not necessarily a physical x-ray source 16a or a physical three-dimensional model 430 (though it may be possible to visualize the three-dimensional model 2430 on the display 2108 in some embodiments). The two-dimensional projections may be rendered at a specified orientation and distance (e.g., an x-ray-source-to-detector distance 2440 or an object-to-detector distance 2450). The spatial relationship of the x-ray source 16a and the three-dimensional model 430 as well as distance(s) 450, 460 may want to be taken into account in certain embodiments to ensure accurate measurements.

In an embodiment, systems and methods of the present disclosure may be used to ensure consistent measurements between radiographic images taken of a patient at a neutral position and radiographic images taken of a patient in a non-neutral (e.g., intra-operative) position without having to ensure that the patient is precisely placed in a neutral position and, potentially, with less x-ray exposure, by simulating movement of the patient back to the neutral position using the three-dimensional model and calculating an adjustment factor taking into account the differences between the actual, non-neutral position of the patient and the patient in a neutral position.

The methods and systems described in the present disclosure may be implemented, at least in part, using certain hardware. For example, referring to FIG. 8, a C-arm apparatus 1001 may capture video or image signals using x-rays. C-arm apparatus 1001 may, for example, capture an intra-operative x-ray image. The C-arm apparatus 1001 may have a display 1002 directly connected to the apparatus to instantly view the images or video. Display 1002 may be configured with a number of various inputs, including, for example, an input to receive one or more data sets of three-dimensional image information. A wireless kit 1010 may, alternatively or additionally, be attached to the C-arm apparatus 1001 via video port 1003 to receive the video or image signal from the C-arm apparatus 1001, the signal representing digital data of a radiographic image frame or plurality of frames. Video port 1003 may utilize a BNC connection, a VGA connection, a DVI-D connection, or an alternative connection known to those of skill in the art. Unique in the field in its ability to convert any wired image acquisition device (such as a C-arm) into a wireless imaging device, the wireless kit 1010 may be the Radlink Wireless C-Arm Kit. Wireless kit 1010 may include a resolution converter 1011 to convert the image signal to proper resolution for further transmission, frame grabber 1012 to produce a pixel-by-pixel digital copy of each image frame, central processing unit 1013, memory 1014, and dual-band wireless-N adapter 1015. The wireless kit 1010 may convert the received signal to one or more image files and can send the converted file(s), for example, by wireless connection 1018 to one or more computer(s) and operatively connected display(s) 1021, 1022.

The computer and operatively connected display may, for example, be a Radlink Galileo Positioning System ("GPS") 1021 or GPS Tablet 1022. The Wireless C-Arm Kit 1010 may receive, convert, and transmit the file(s) in real time. The methods described in the present disclosure may be implemented, for example, as software running on the GPS 1021 or GPS Tablet 1022 units. The GPS 1021 and GPS Tablet 1022 may also incorporate additional functions, such as those provided in the Radlink Pro Imaging with Surgeon's Checklist software.

While various aspects and embodiments have been disclosed herein, other aspects and embodiments will be apparent to those skilled in the art. The various aspects and embodiments disclosed herein are for purposes of illustration and are not intended to be limiting.

What is claimed is:

1. A method of generating a three dimensional image from a composite intra-operative radiographic image comprising:
    iteratively registering a plurality of two-dimensional projections of a portion of a patient from a three-dimensional model of the portion of the patient, the three-dimensional model being generated from a data set of imaging information obtained at a neutral position, and each two-dimensional projection having a spatial orientation;
    receiving a plurality of sequential radiographic image frames pertaining to a patient from a single X-ray detector;
    cropping the image frames to create cropped image frames; and
    stitching together in a sequential order a plurality of selected portions of the cropped image frames as a composite intra-operative radiographic image, wherein the selected portions are selected according to a method comprising:
        selecting a sequentially first portion from a first cropped image frame as a first selected portion;
        applying image registration without using artificial markers;
        selecting one or more interior portions from one or more of cropped image frames occurring sequentially later than the first cropped image frame as interior selected portions, wherein each interior selected portion is not otherwise altered or adjusted for geometric distortion;
        selecting a sequentially last portion from a last cropped image frame as a last selected portion
    scoring each two-dimensional projection against the intra-operative image by determining a best fit of each projection to the intra-operative image and calculating a spatial difference between corresponding points;
    identifying a global minimum score reflecting the smallest spatial difference between the corresponding points on the two-dimensional projection and the intra-operative image and selecting the two-dimensional projection having the global minimum score as an intra-operative projection;
    obtaining values representing the orientation of the three-dimensional model corresponding to the intra-operative projection; and
    calculating an adjustment factor based on the difference in the values representing the orientation of the three-dimensional model at the intra-operative projection position and values representing the orientation of the three-dimensional model at the neutral position.

2. The method of claim 1, wherein the stitching step includes aligning at least one edge of each of the plurality of selected portions of cropped image frames with an edge of another of the plurality of selected portions of cropped image frames to generate an image of the region of interest that corrects effects of parallax distortion.

3. The method of claim 1, wherein the dimension of each interior selected portion is equal to the measured displacement.

4. The method of claim 1, wherein each interior selected portion is taken from the interior 25% of the respective cropped image frame.

5. The method of claim 1, further comprising identifying a reference point on the intra-operative image using one of a canny edge detector algorithm, a shape-based segmentation algorithm, manual selection, and a combination thereof.

6. The method of claim 1, wherein the three-dimensional model of the portion of the patient is generated by applying one of a region grow algorithm, a water shed algorithm, an active contour algorithm, and a combination thereof to the data set of imaging information.

7. The method of claim 1, wherein the measuring step comprises applying intensity-based image registration using a gradient descent algorithm.

8. A method of generating a three-dimensional image from intra-operative radiographic imaging information comprising:
    receiving a data set of imaging information representing at least a first portion of a patient in a neutral position;
    generating a three-dimensional model of the first portion of the patient based on the data set of imaging information;
    receiving a plurality of sequential anteroposterior radiographic image frames pertaining to a patient from a single X-ray detector;

identifying a region of interest on each of the image frames;

cropping the identified region of interest from a plurality of the image frames to create cropped image frames; and stitching together a plurality of selected portions of cropped image frames, wherein the plurality of selected portions of cropped image frames is selected according to a method comprising:

selecting a sequentially first portion from a first cropped image frame;

executing an iterative process to select a plurality of interior portions, the process including:

applying intensity-based image registration using a gradient descent algorithm on anatomical landmarks without using artificial markers;

measuring a displacement with respect to a longitudinal axis of the region of interest between each pair of sequentially adjacent cropped image frames;

selecting an interior portion from the sequentially later cropped image frame, wherein the selected portion is not otherwise altered or adjusted for geometric distortion, and has a dimension equal to the measured displacement;

selecting a sequentially last portion from a last cropped image frame;

identifying a bony edge contour in the intra-operative imaging information;

iteratively rendering a plurality of two-dimensional projections from the three-dimensional model, each two-dimensional projection having a corresponding spatial orientation;

scoring each two-dimensional projection by calculating the distance of the bony edge contour in the intra-operative imaging information to a corresponding contour in each two-dimensional projection and identifying a global minimum score;

outputting a transformation matrix for the two-dimensional projection having the global minimum score, the transformation matrix representing the orientation of the three-dimensional model relative to the neutral position when the two-dimensional projection having the global minimum score was rendered; and calculating an adjustment factor based on the transformation matrix.

9. The method of claim 8, wherein the stitching step includes aligning at least one edge of each of the plurality of selected portions of cropped image frames with an edge of another of the plurality of selected portions of cropped image frames to generate an image of the region of interest that corrects effects of parallax distortion.

10. The method of claim 8, wherein the plurality of anteroposterior radiographic image frames is generated from a plurality of discrete radiographic exposures.

11. The method of claim 8, wherein each interior selected portion is taken from the interior 25% of the respective cropped image frame.

12. The method of claim 8, wherein the measuring step comprises applying intensity-based image registration using a gradient descent algorithm.

13. The method of claim 8, further comprising identifying a reference point on the intra-operative image using one of a canny edge detector algorithm, a shape-based segmentation algorithm, manual selection, and a combination thereof.

14. The method of claim 8, wherein the three-dimensional model of the portion of the patient is generated by applying one of a region grow algorithm, a water shed algorithm, an active contour algorithm, and a combination thereof to the data set of imaging information.

15. A system for generating a three-dimensional image from intra-operative imaging information that corrects effects of parallax distortion comprising:

a C-arm including an x-ray source and x-ray detector disposed thereon;

a computer communicatively coupled to the C-arm including a display, a receiver, and a microcontroller operatively coupled to the display and to the receiver and having access to a non-transitory memory, the system memory including software instruction causing the microcontroller to:

receive a data set of imaging information representing at least a first portion of a patient in a neutral position;

generate a three-dimensional model of the first portion of the patient based on the data set of imaging information;

receive a plurality of sequential radiographic image frames pertaining to a patient from a single X-ray detector;

identify a region of interest on each of the image frames;

crop the identified region of interest from a plurality of the image frames to create cropped image frames; and stitch together in a sequential order a plurality of selected portions of the cropped image frames, wherein the selected portions are selected according to an algorithm comprising the steps of:

selecting a sequentially first portion from a first cropped image frame;

executing an iterative process to select a plurality of interior portions, the process including:

applying intensity-based image registration using a gradient descent algorithm on anatomical landmarks without using artificial markers;

measuring a displacement with respect to a longitudinal axis of the region of interest between each pair of sequentially adjacent cropped image frames;

selecting an interior portion from the sequentially later cropped image frame, wherein the selected portion is not otherwise altered or adjusted for geometric distortion, and has a dimension equal to the measured displacement; and selecting a sequentially last portion from a last cropped image frame identify a bony edge contour in the intra-operative imaging information;

iteratively render a plurality of two-dimensional projections from the three-dimensional model, each two-dimensional projection having a corresponding spatial orientation;

scoring each two-dimensional projection by calculating the distance of the bony edge contour in the intra-operative imaging information to a corresponding contour in each two-dimensional projection and identify a global minimum score;

output a transformation matrix for the two-dimensional projection having the global minimum score, the transformation matrix representing the orientation of the three-dimensional model relative to the neutral position when the two-dimensional projection having the global minimum score was rendered;

calculate an adjustment factor based on the transformation matrix; and output to the display a visual indication of an intra-operative adjustment to be made to a component based on the adjustment factor to achieve a target component orientation.

16. The system of claim 15, wherein the instructions further cause the processor to align at least one edge of each of the plurality of selected portions of cropped image frames with an edge of another of the plurality of selected portions of cropped image frames to generate an image of the region of interest that corrects effects of parallax distortion.

17. The system of claim 15, wherein each selected interior portion is taken from the interior 25% of the respective cropped image frame.

18. The system of claim 15, further comprising identifying a reference point on the intra-operative image using one of a canny edge detector algorithm, a shape-based segmentation algorithm, manual selection, and a combination thereof.

19. The system of claim 15, wherein the three-dimensional model of the portion of the patient is generated by applying one of a region grow algorithm, a water shed algorithm, an active contour algorithm, and a combination thereof to the data set of imaging information.

20. The system of claim 15, wherein the measuring step of the algorithm comprises applying intensity-based image registration using a gradient descent algorithm.

* * * * *

UNITED STATES PATENT AND TRADEMARK OFFICE
CERTIFICATE OF CORRECTION

Page 1 of 1

PATENT NO. : 10,748,319 B1
APPLICATION NO. : 16/851545
DATED : August 18, 2020
INVENTOR(S) : Wenchao Tao, Ning Xuan and Roy Davidovitch It is certified that error appears in the above-identified patent and that said Letters Patent is hereby corrected as shown below:

On the Title Page

Item (72), should be changed from:
-- Wenchao Tao, Los Angeles, CA (US); Ning Xuan, Torrance, CA (US) --
To:
-- Wenchao Tao, Los Angeles, CA (US); Ning Xuan, Torrance, CA (US); Roy Davidovitch, Tenafly, NJ (US) --

Signed and Sealed this
Fifteenth Day of June, 2021

Drew Hirshfeld
*Performing the Functions and Duties of the
Under Secretary of Commerce for Intellectual Property and
Director of the United States Patent and Trademark Office*